United States Patent [19]
Müller et al.

[11] Patent Number: 5,740,224
[45] Date of Patent: Apr. 14, 1998

[54] CONE BEAM SYNTHETIC ARRAYS IN THREE-DIMENSIONAL COMPUTERIZED TOMOGRAPHY

[75] Inventors: Martin Müller, Fellbach, Germany; Gonzalo R. Arce, Wilmington, Del.; Robert A. Blake, Jr., Apollo, Pa.

[73] Assignees: University of Delaware, Newark, Del.; Aluminum Co. of America, Pittsburgh, Pa.

[21] Appl. No.: 564,854

[22] Filed: Nov. 30, 1995

Related U.S. Application Data

[63] Continuation-in-part of Ser. No. 313,735, Sep. 27, 1994, abandoned.

[51] Int. Cl.$^6$ .................................................. L01N 23/083
[52] U.S. Cl. .................................. 378/11; 378/20; 378/901
[58] Field of Search ........................ 364/413.15; 378/901, 378/20, 15, 11, 10, 8, 4

[56] References Cited

U.S. PATENT DOCUMENTS

| | | | |
|---|---|---|---|
| 4,128,877 | 12/1978 | Katz | 364/414 |
| 4,212,062 | 7/1980 | Kohno et al. | 364/414 |
| 4,558,458 | 12/1985 | Katsumata et al. | 378/20 |
| 4,600,998 | 7/1986 | Huet | 364/507 |
| 4,989,225 | 1/1991 | Gupta et al. | 378/10 |
| 5,032,990 | 7/1991 | Eberhard et al. | 364/413.15 |
| 5,046,003 | 9/1991 | Crawford | 364/413.15 |
| 5,090,401 | 2/1992 | Schwieker | 128/24 |
| 5,164,971 | 11/1992 | Peyret et al. | 378/4 |
| 5,187,659 | 2/1993 | Eberhard et al. | 364/413.15 |
| 5,210,688 | 5/1993 | Cheu et al. | 364/413.19 |
| 5,270,926 | 12/1993 | Tam | 364/413.19 |
| 5,319,693 | 6/1994 | Eberhard et al. | 378/19 |
| 5,390,112 | 2/1995 | Tam | 364/413.15 |

FOREIGN PATENT DOCUMENTS

WO 92/03970   3/1992   WIPO ........................ 378/4

*Primary Examiner*—David P. Porta
*Assistant Examiner*—David Vernon Bruce
*Attorney, Agent, or Firm*—Connolly & Hutz

[57] ABSTRACT

The method of the present invention combines an ensemble of truncated partial cone beam projections to synthesize a complete virtual projection. The individual partial projections are obtained with CT scanners, where for each partial projection the investigated object is positioned at precise locations specified by formulas described in the present application (e.g., formulas (3), (4), (6) and (18) for linear cone beam synthetic scanner arrays or formulas (9)–(13), (20), (21) and (25)–(27) for circular cone beam synthetic scanner arrays). Prior to the actual reconstruction, the partial cone beam projections are combined to form a complete virtual projection, equivalent to a projection one would obtain by using a sufficiently large detector.

12 Claims, 30 Drawing Sheets

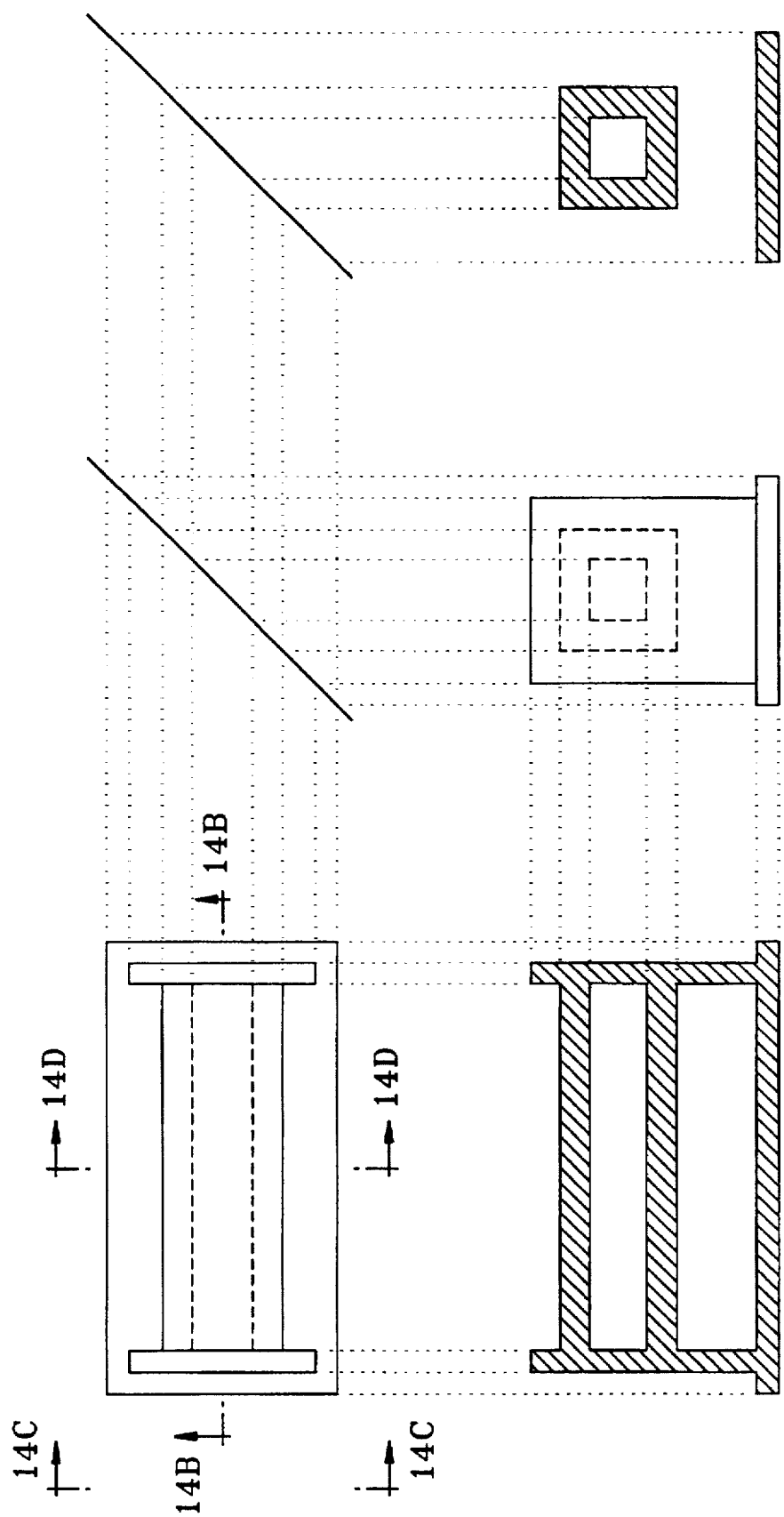

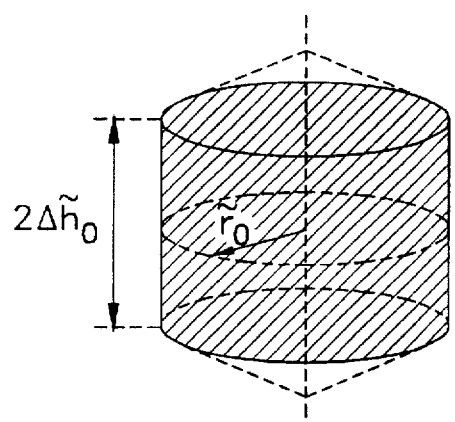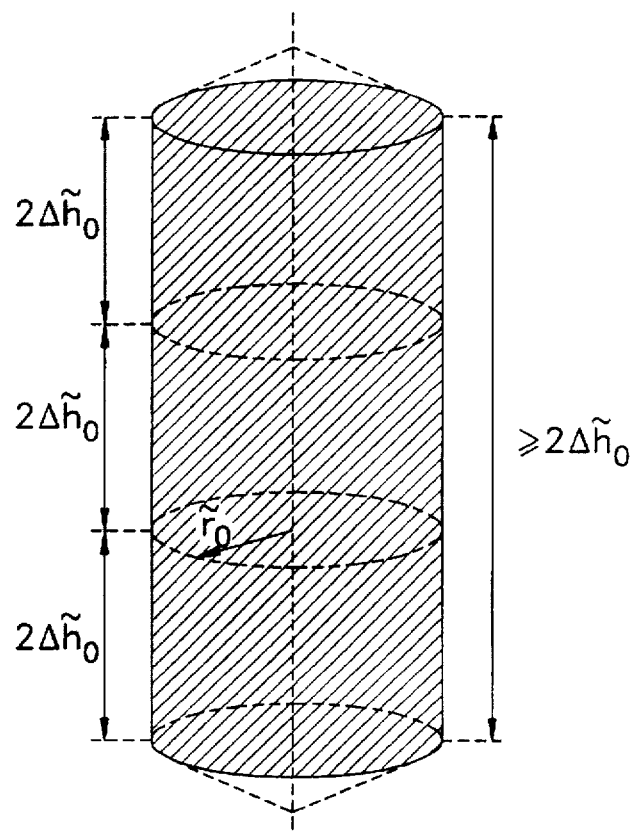
FIG. 18A
FIG. 18B

CONE BEAM SYNTHETIC ARRAYS IN THREE-DIMENSIONAL COMPUTERIZED TOMOGRAPHY

CROSS-REFERENCE TO RELATED APPLICATIONS

The present patent application is a continuation-in-part application of Ser. No. 08/313,735 filed on Sep. 27, 1994, now abandoned, in the names of Müller et al.

BRIEF DESCRIPTION OF THE INVENTION

The method of the present invention combines an ensemble of truncated partial cone beam projections to synthesize a complete virtual projection. The individual partial projections are obtained with CT scanners, where for each partial projection the investigated object is positioned at precise locations specified by formulas described hereinafter (i.e., formulas (3), (4), (6) and (18) for linear cone beam synthetic scanner arrays or formulas (9)–(13), (20), (21) and (25)–(27) for circular cone beam synthetic scanner arrays). Prior to the actual 3-dimensional reconstruction, the partial cone beam projections are combined to form a complete virtual projection, equivalent to a projection one would obtain by using a sufficiently large detector.

BACKGROUND OF THE INVENTION

Computerized tomography (CT) is an advanced method of nondestructive evaluation (NDE) employed in medical imaging, material science, quality assurance, etc. An image is recovered from projection data obtained with a CT scanner through a reconstruction algorithm. The CT scanner consists of a source (usually emitting X-rays), a detector, and a turntable positioned between the source and the detector. The object to be investigated is placed onto the turntable and is rotated 360° while the projection data (i.e., the X-ray shadow) is recorded. FIGS. 1A and 1B illustrate the scanner setup for 2D and 3D CT. Standard reconstruction methods recover images from objects whose projections fall entirely within the detector boundaries. In 2D CT, a slice of the object representing the fan beam plane of projection through the object is recovered. In 3D CT, the entire volume of the object representing the cone beam space of projection of the object is recovered. Truncated projections due to oversize objects, as depicted in FIGS. 2A and 2B, result in severe artifacts in the reconstructed image, degrading the entire image and making those portions of the object whose projections fall outside of the detector limits unidentifiable. Since size and shape of the investigated object necessarily depends on the specific application, a detector large enough to guarantee complete projection of the largest possible object to be investigated has to be made available. This approach is both expensive and uneconomical. Methods of two-dimensional tomographic reconstruction from partial scans, which are recorded with detectors substantially smaller than the investigated object, have been proposed, as in U.S. Pat. No. 5,032,990 (J. W. Eberhard, General Electric Company, New York), for instance. Methods for three-dimensional partial scanning, however, are not yet available.

The size range of commercial detectors is limited due to manufacturing and cost constraints. A method allowing reconstruction of large objects in 3D CT using smaller detectors with a minimum cost in added hardware would extend the feasibility of 3D CT scanners and increase the range of applications in material science and quality assurance (investigation of large profiles, car parts, parts of airplane wings, etc).

Currently, a method allowing artifact-free reconstruction of oversize objects with small detectors in 3D CT does not exist. Existing methods dealing with reconstruction from truncated projections are limited to two-dimensional (2D) CT. Suboptimal software-only solutions, which may be (but have not been) extended from 2D CT to 3D CT will not approach the quality of the hardware/software method of the present invention. Furthermore, the existing methods for 2D CT fail if a significant portion of the projections is lost. Similar problems can be expected for an extension to 3D CT. The method of the present invention allows arbitrary extension of the physical detector limits, and offers artifact-free reconstruction for any degree of truncation. The resulting images are comparable to the images obtained with a single (large) cone beam scanner.

SUMMARY OF THE INVENTION

The method of the present invention combines an ensemble of truncated partial cone beam projections to synthesize a complete virtual projection. The individual partial projections are obtained with cone-beam CT scanners, where for each partial projection the investigated object is positioned at precise locations specified by formulas set forth hereinafter (i.e., formulas (3), (4), (6) and (18) for linear cone beam synthetic scanner arrays or formulas (9)–(13), (20), (21) and (25)–(27) for circular cone beam synthetic scanner arrays). Prior to the actual reconstruction, the partial cone beam projections are combined to form a complete virtual projection, equivalent to a projection one would obtain by using a sufficiently large detector. Although both the physical (small) detectors as well as the virtual (large) detector usually use a uniform sensor element spacing, the various object displacements necessitated by the method of the present invention and the divergent geometry of cone beam projections require the virtual projection data to be synthesized by interpolation.

There are two preferred methods of the present invention (i.e. circular cone beam synthetic scanner arrays and linear cone beam synthetic scanner arrays). The two methods differ in that they use different object displacements, a different algorithm for synthesizing the virtual projection data, and a different reconstruction algorithm to recover an image of the object from the virtual projection data. Either method, however, uses a standard cone beam scanner to record the truncated partial cone beam projections. According to the arrangement of the physical detectors governed by the various object displacements in the method of the present invention, the methods are called circular cone beam synthetic scanner arrays and linear cone beam synthetic scanner arrays. Each of the methods is described below.

BRIEF DESCRIPTION OF THE DRAWINGS

FIG. 5(A) shows a simulated object; FIG. 5(B) shows a reconstruction from 1 partial scan; FIG. 5(C) shows a reconstruction from 3 partial scans and FIG. 5(D) shows a reconstruction from 5 partial scans. The object under inspection is covered by 5 partial scans (i.e., complete reconstruction without truncation artifacts).

FIG. 11(A) shows the scanned object. The dashed circles delimit the virtual artifact-free zones obtained with 1, 3, and 5 scanners/partial sets of projections for N=0, N=1, and N=2, respectively. FIG. 11(B) shows the reconstruction from 1 partial set of projections. FIG. 11(C) shows the reconstruction from 3 partial sets of projections. FIG. 11(D) shows the reconstruction from 5 partial sets of projections.

FIG. 12(A) shows a cut along the y-axis. Parameter $\zeta_o$ denotes the vertical detector size.

FIGS. 14(A–D) show a schematic graph of an object wherein the grey regions in the object correspond to densities $\rho$=1.0.

FIG. 15 shows the wedge beam geometry wherein

FIG. 16(A) shows the simulated object; FIG. 16(B) shows a reconstruction from center scan; FIG. 16(C) shows a reconstruction from 3 partial scans and FIG. 16(D) shows a reconstruction from 5 partial scans.

FIGS. 18A and B show the vertical extension of the virtual artifact-free zone due to synthetic scanner arrays. The shaded regions depict the cylindrical portion of the artifact-free zone. Specifically, FIG. 18(A) shows a single slice virtual artifact-free zone and FIG. 18(B) shows a stacking of multiple slices for M=3.

FIG. 19(A) shows a top view wherein the circle with radius $\tilde{r}_o$ delimits the horizontal extend of the artifact-free zone and FIG. 19(B) is a graph depicting a geometrical identity in linear scanner arrays.

DETAILED DESCRIPTION OF THE INVENTION

Figure 1A:
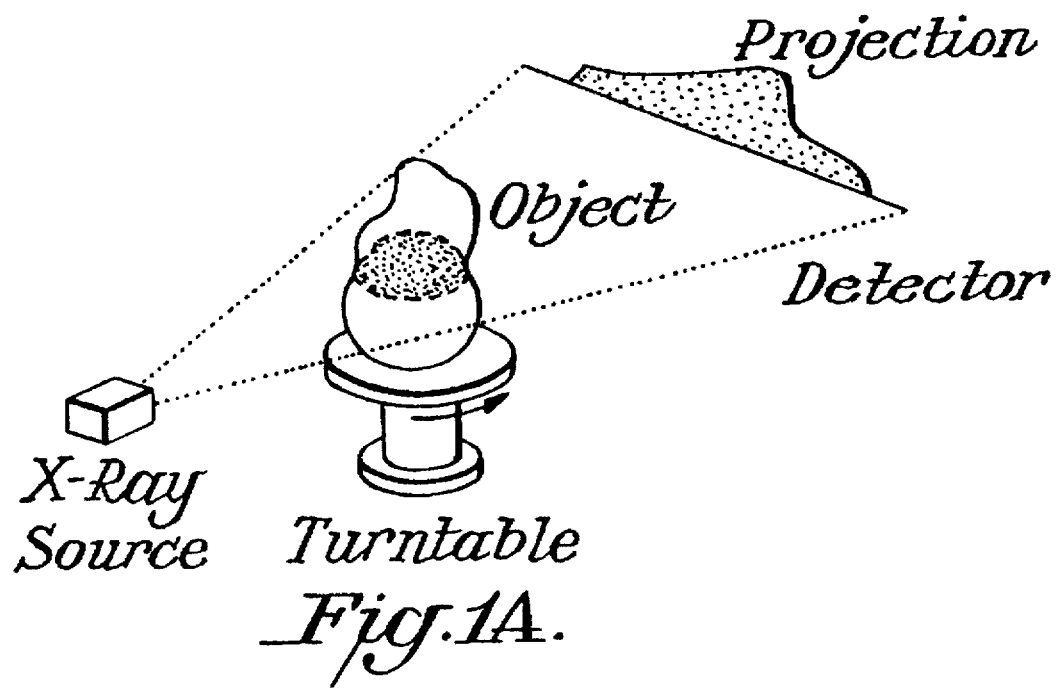
FIG. 1A shows the scanner setup for two dimensional computerized tomography. The detector has the form of a straight line, recording the fan beam projection of a two-dimensional slice of the object.
Figure 1B:
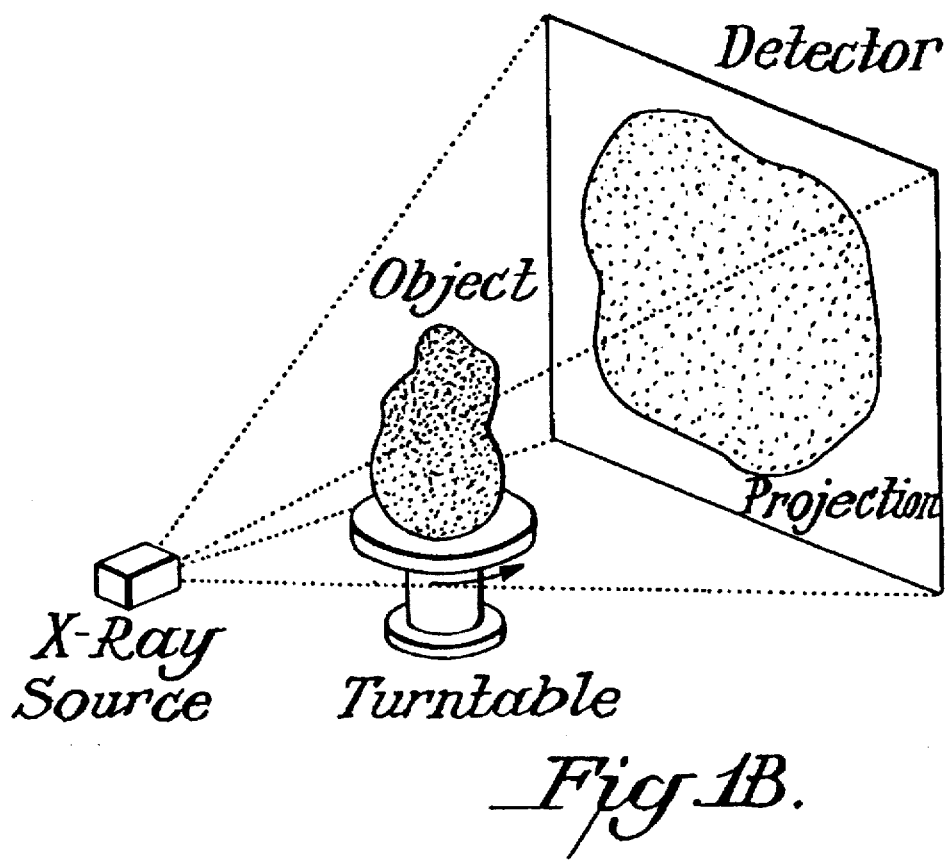
FIG. 1B shows the scanner setup for three dimensional computerized tomography. The detector has the form of a plane, recording the cone beam projection of the entire object.
Figure 2A:
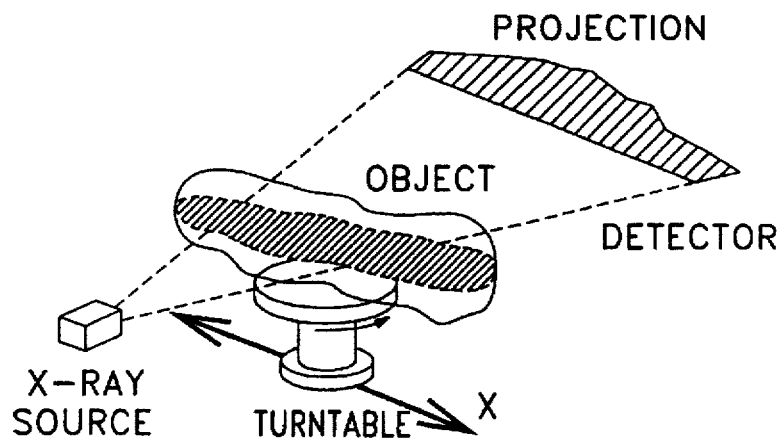
FIG. 2A shows a scanner setup for two dimensional computerized tomography wherein portions of the object to be examined extend beyond the detector limits, thus resulting in truncated projections.
Figure 2B:
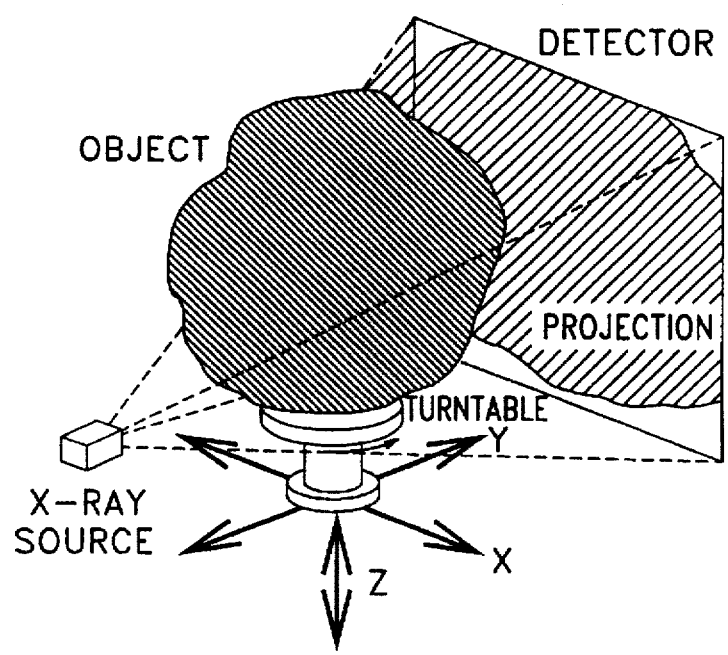
FIG. 2B shows a scanner setup for three dimensional computerized tomography wherein portions of the object to be examined extend beyond the detector limits, thus resulting in truncated projections.

The method of circular cone beam synthetic scanner arrays arranges the physical 3D CT cone beam detectors in a circular fashion around the cone beam source, such that the physical detectors form a circular dome covering the investigated object. The object is placed on a turntable located between the x-ray source and the physical detectors. The turntable should be able to rotate the object 360° with respect to the source and detector and move the object horizontally along the two linear axes (X,Y) (See FIG. 2B). In a preferred embodiment, the turntable should also be able to move the object vertically (along the Z-axis). As evident from FIG. 3, the projection on the virtual detector is found by extending the projection rays incident on the physical detectors onto the virtual detector. Since the uniform sensor grid on the virtual detector does not necessarily conform to the uniform sensor grid on the physical detectors when extended onto the virtual detector, interpolation is necessary to determine the projection intensities at the sensor elements on the virtual detector. Once the complete virtual projection data is synthesized from the truncated partial projections, an image of the investigated object may be reconstructed. Since the virtual projection data is equivalent to a single cone beam projection recorded with a detector sufficiently large to cover the projection of the entire object, the reconstruction can be carried out with a standard cone beam algorithm such as the widely used cone beam convolution back projection method by Feldkamp, for instance. The algorithm combining the partial projections is implemented in software and usually executes in a fraction of the time required to reconstruct the image. In practice, one would keep the physical detector stationary, while the turntable rotating the object is displaced and prerotated such that it assumes the appropriate position relative to the source and detector to simulate a given segment of the dome of detectors shown in FIG. 3. Thus, the ensemble of truncated partial projections is obtained by a series of displacements and recordings, rather than by actually arranging the detectors around the object. The construction of the synthetic projection data may begin as soon as the first partial projection has been recorded.

For 3D CT, approximate reconstruction methods such as Feldkamp's method are used in practice, due to the complexity and excessive runtime of exact reconstruction methods. Furthermore, the standard cone beam projection geometry does not yield projections sufficiently describing the object. Instead, it yields information almost completely describing the projected object, with the object description becoming less accurate as the vertical cone spread angle increases. Provided that the vertical cone beam spread angle does not exceed a certain limit, however, the error introduced in the image by the cone beam projection geometry and the approximate reconstruction methods is negligible, indistinguishable from image noise, and undetectable by the human eye.

Figure 4:
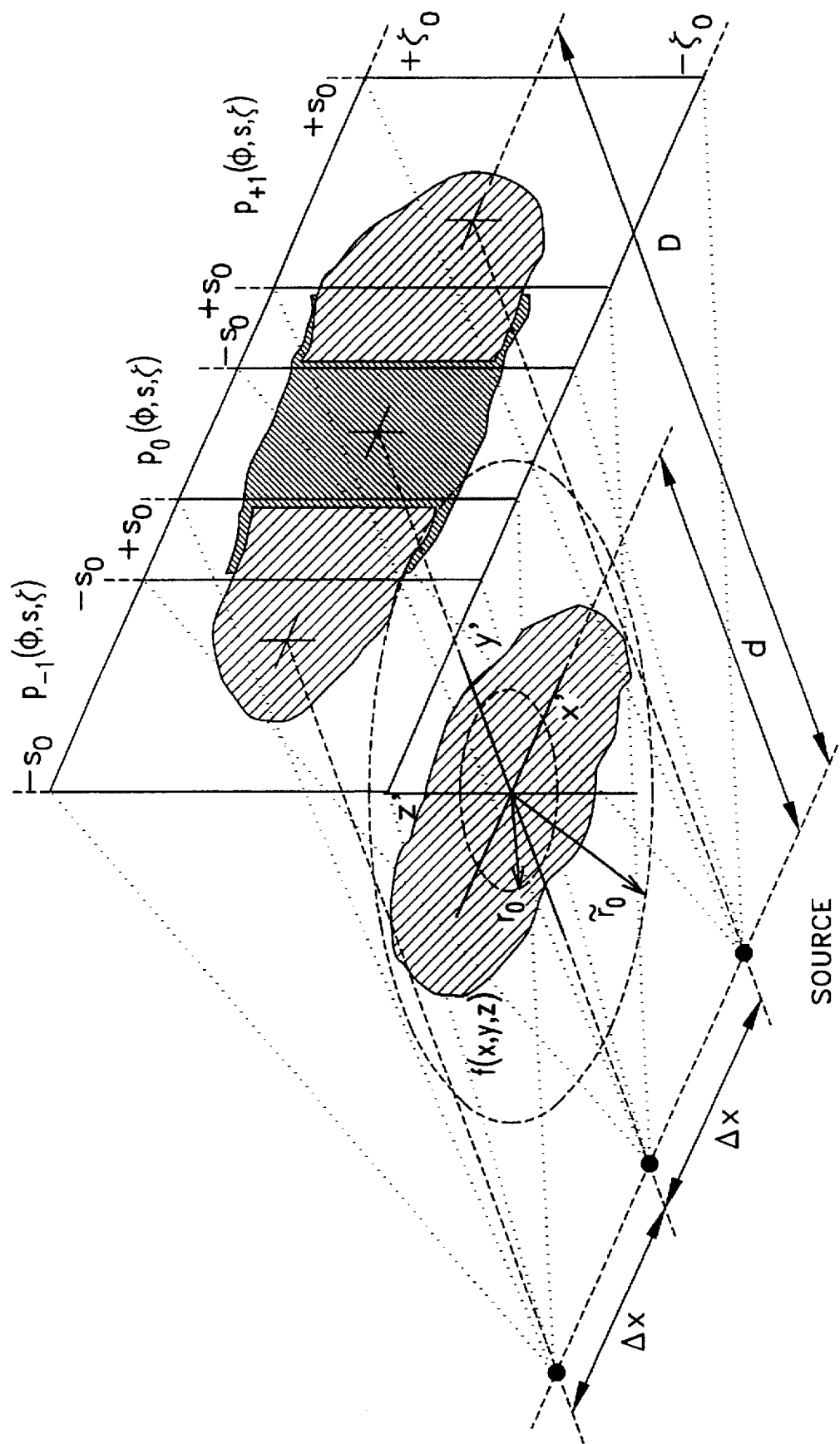
FIG. 4 shows a linear cone beam scanner array. Parameters D and d denote the source-to-detector and the source-to-object distances, respectively, while $\pm s_o$ and $\pm \zeta_o$ denote the detector size. Parameter $r_o$ denotes the radius of the artifact-free zone for the center cone beam scanner, while $\tilde{r}_o$ denotes the radius of the virtual artifact-free zone obtained from 3 partial cone beam scanners with displacements $\Delta_{s,x}$ (shown as $\Delta x$ in FIG. 4).
Figure 5A:
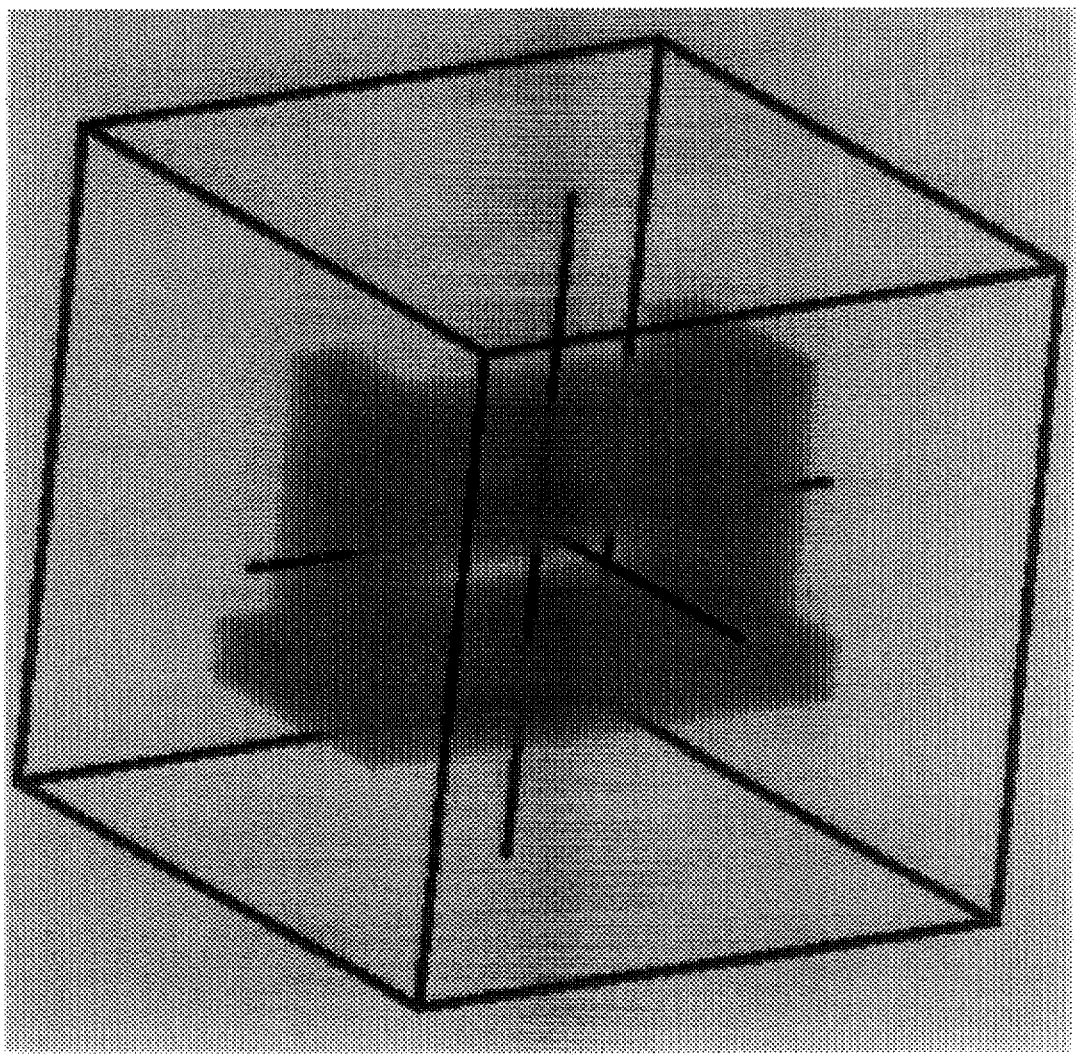
FIGS. 5A–D show volumetric images of reconstructions from virtual sets of cone beam projections, resorted from partial cone beam scans due to a circular synthetic scanner array. The bright regions in the images depict artifacts.
Figure 5B:
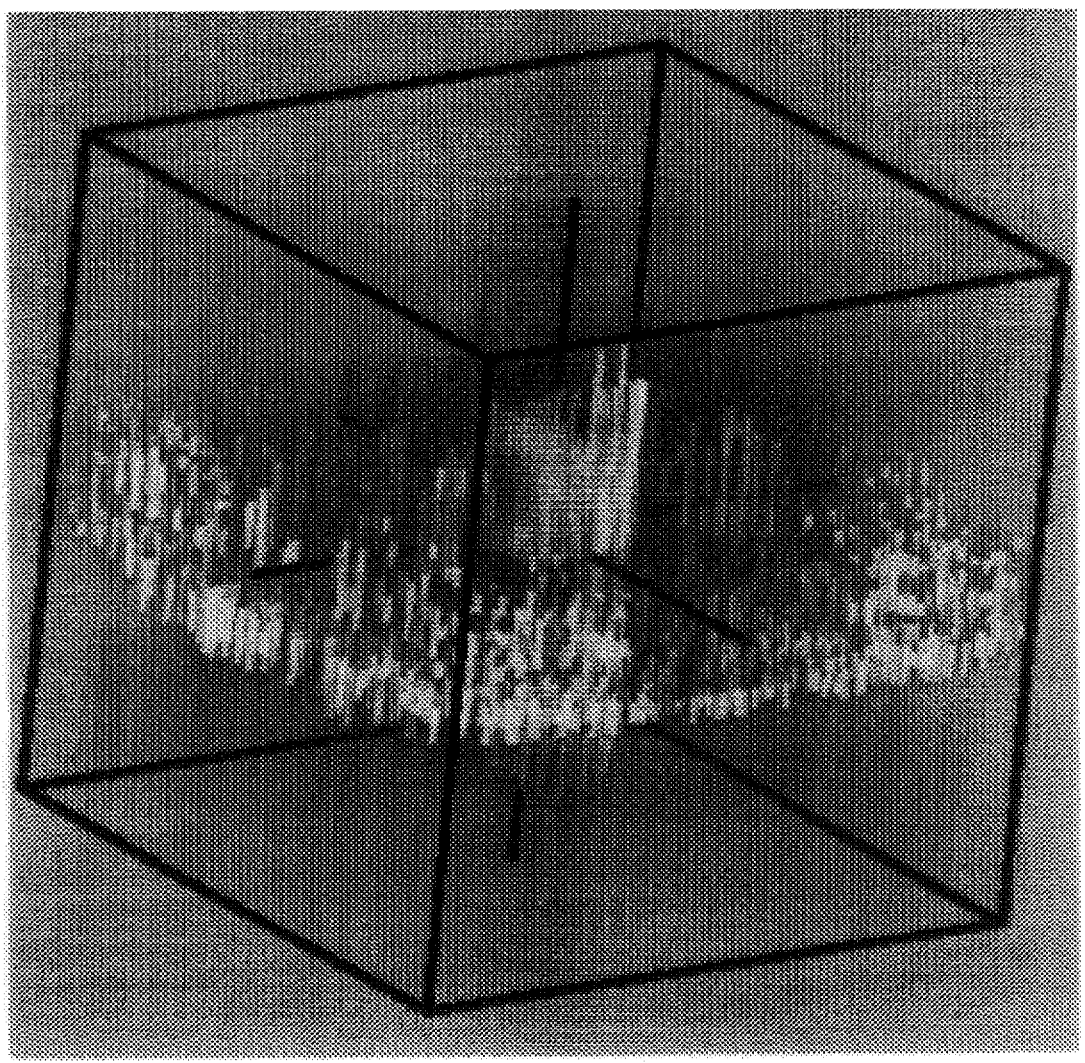
Figure 5C:
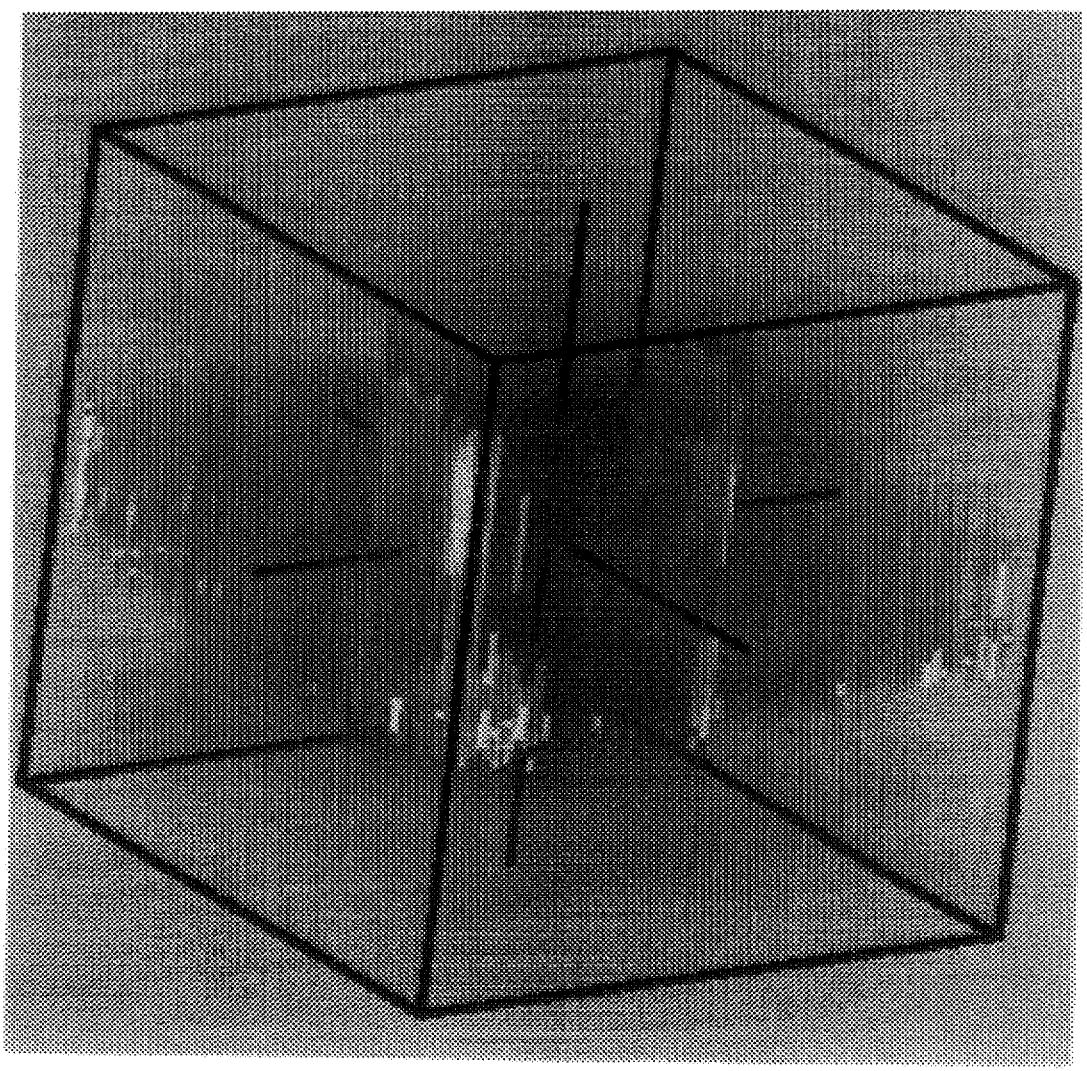
Figure 5D:
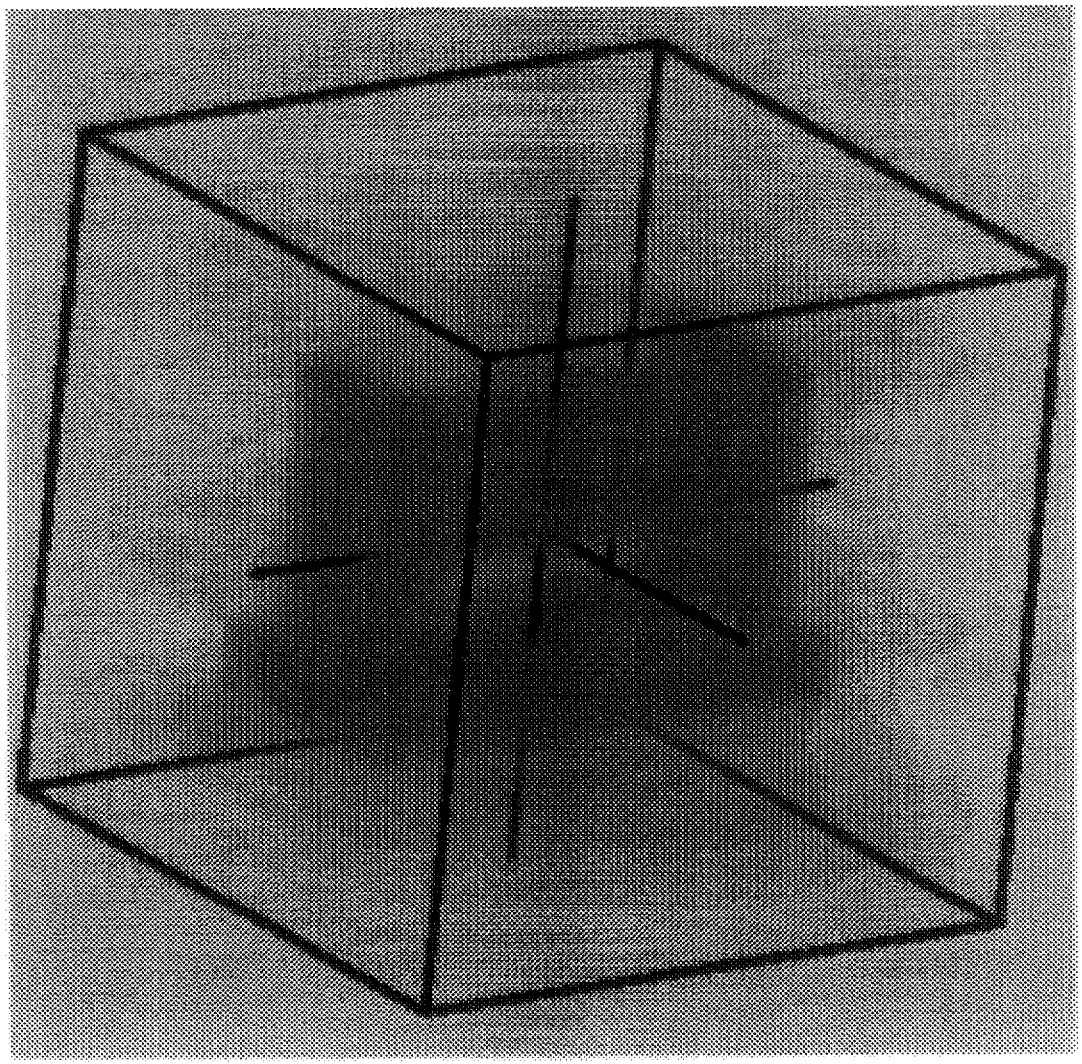

The method of linear cone beam synthetic scanner arrays is less straightforward than the previously described method. The object displacements, however, are simpler to implement since they occur strictly parallel to the virtual detector as shown in FIG. 4. The object is placed on a turntable located between the x-ray source and the physical detectors. The turntable should be able to rotate the object 360° with respect to the source and detector and move the object horizontally along one linear axis (X) (see FIG. 2B). In a preferred embodiment, the turntable should also be able to move the object vertically (along the Z-axis). As has been shown in a tedious mathematical exercise, partial projections recorded with linear displacements cannot be used to synthesize a virtual cone beam projection, as has been done in the previously described method. Thus, a specialized resorting algorithm which rebins the partial cone beam projections into a virtual wedge beam projection needs to be employed. Although the wedge beam rebinning uses interpolation as used in the previously described method (i.e., the circular cone beam synthetic scanner arrays method), additional preprocessing is required to perform source jitter compensation to reduce the image error attributed to the rebinning step. The nature of this compensation is rather complex and is thus not described here in detail. However, the following paragraph is provided as a general description of source jitter compensation.

Figures 7, 9:
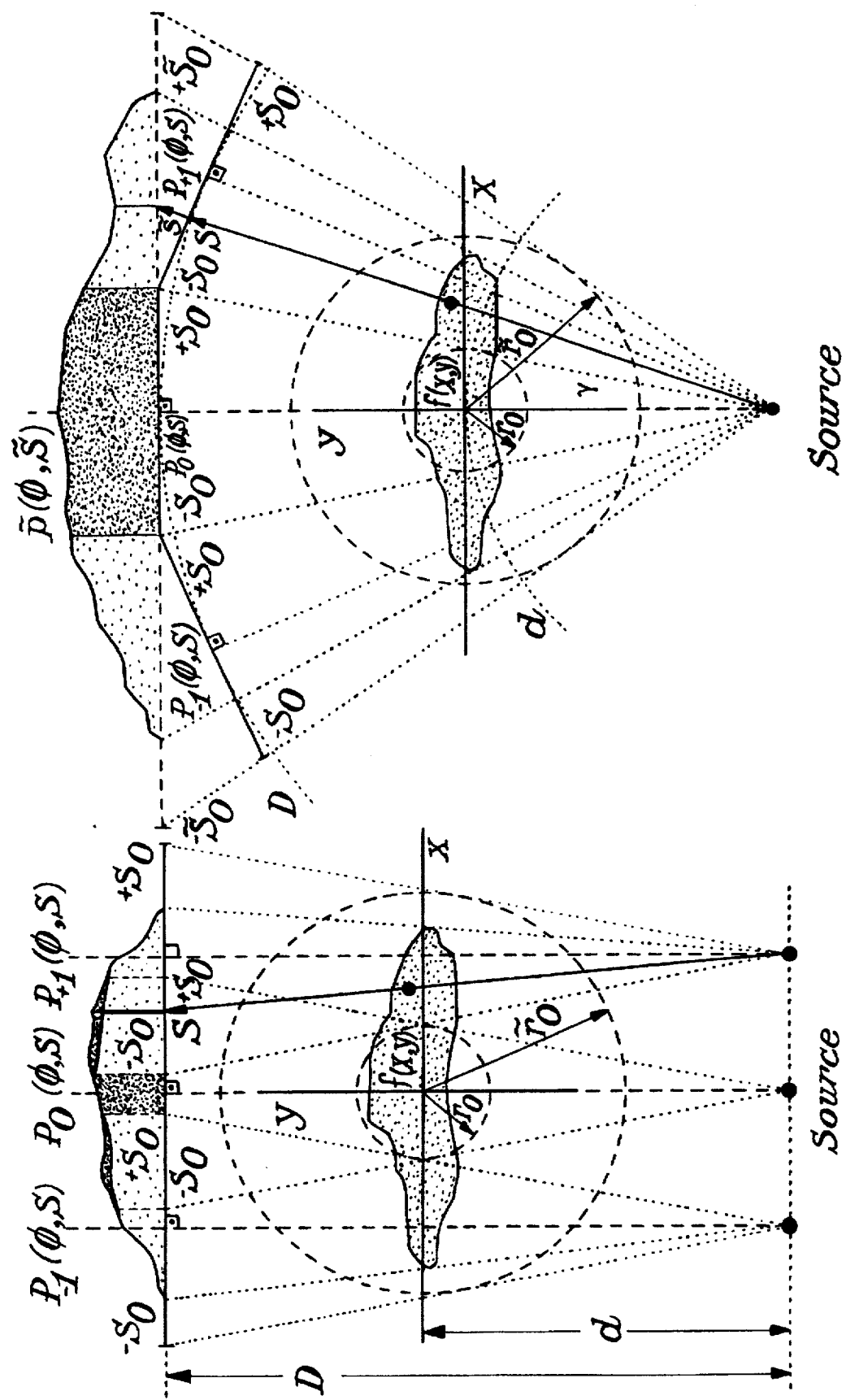
FIG. 7 shows a linear array of fan beam scanners. The 3 physical source-detector arrangements have identical parameters D; d and $s_o$, and differ only in their horizontal displacement. The dashed circle of radius $r_o$ delimits the artifact-free zone as obtained with a single scanner, while $\tilde{r}_o$ denotes the radius of the virtual artifact-free zone. The light shaded regions depict the partial projections supplementing the set of projections obtained with the center scanner.
FIG. 9 shows a circular array of fan beam scanners. The 3 physical source-detector arrangements have identical parameters D, d, and $s_o$, and differ only in their tilt angles. The dashed circle with radius $r_o$ delimits the artifact-free zone as obtained with a single scanner, while $\tilde{r}_o$ denotes the radius of the virtual artifact-free zone of the circular array of scanners. The light shaded tails in the virtual projection $\tilde{p}(\phi,\tilde{s})$ depict the regions outside the range of the center scanner.
Figure 15A:
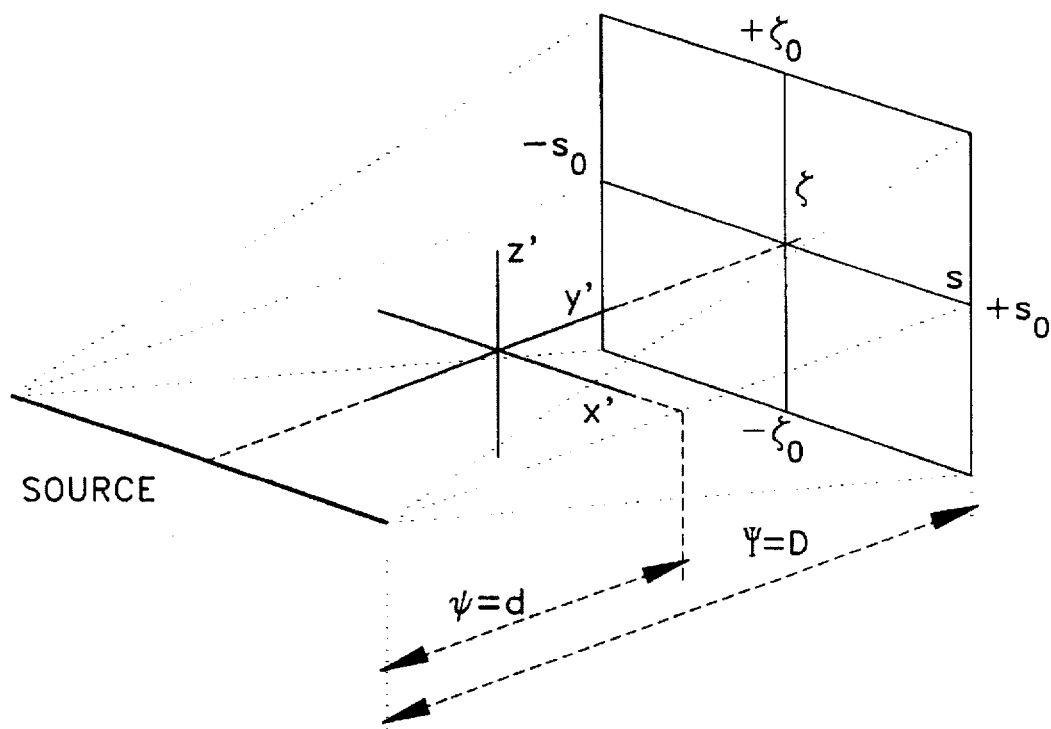
FIG. 15(A) is the ideal wedge beam geometry and FIG. 15(B) is the source-to-object distance $\psi$ as a function of the ray displacement $\tau$ for 5 partial sets of cone beam projections with parameters D=10, d=5 and $s_o$=1. The horizontal dashed line depicts the source-to-object distance d.

From FIG. 9, it can be seen that for a circular synthetic scanner array both the ensemble of physical (small) cone beam scanners forming a dome around the investigated object, and the virtual (large) cone beam scanner share the exact same source location. For linear synthetic scanner arrays using a wedge beam reconstruction, this is no longer true. While the ensemble of linearly displaced physical (small) cone beam scanners use point sources at distinct locations, the virtual (large) wedge beam scanner ideally requires a straight line source, as depicted in FIG. 15A. Resorting the ensemble of linearly displaced cone beam projections from a linear synthetic scanner array, however, yields a source locus according to FIG. 15B. Since the ratio of the source-to-object distance versus the source-to-detector distance determines the magnification of the projection on the detector plane, and for an ensemble of projections from a linear synthetic scanner array resorted into a virtual wedge beam projection the source-to-object distance varies and contains discontinuities, image artifacts result at those image locations associated with the discontinuities in the virtual wedge beam projection. Source jitter compensation reduces these reconstruction artifacts by keeping the source-to-object versus source-to-virtual detector ratio constant (i.e., adjust the source-to-virtual detector distance for any point along the horizontal axis of the virtual detector). Thus, discontinuities are avoided for a cross-section of the investigated object parallel to the virtual detector located at the axis of object rotation. For object cross-sections closer or further from the source, projection discontinuities and subsequently image artifacts cannot be completely cancelled. However, they are substantially reduced.

The geometry of the synthesized wedge beam projection is depicted in FIG. 15(A). For reconstruction from the virtual wedge beam data, a specialized wedge beam reconstruction algorithm had to be developed. As already mentioned for Feldkamp's cone beam reconstruction method, the wedge beam reconstruction method employs similar approximations when recovering the image. The image error introduced by the new wedge beam algorithm is comparable to the error introduced by Feldkamp's method, and substantially stems from the inherent inaccuracies of the partial cone beam projections rather than algorithm insufficiencies. The algorithm combining the partial projections is implemented in software and usually executes in a fraction of the time required to reconstruct the image. In it's practical application, the method of linear cone beam synthetic scanner arrays is almost identical to the previously described method. Keeping the physical detector stationary, the turntable rotating the object is displaced and prerotated such that it assumes the appropriate position relative to the source and detector to simulate a given segment of the virtual detector as shown in FIG. 4. Thus, the ensemble of truncated partial projections is obtained by a series of displacements and recordings, rather than by actually arranging the detectors along the object. The construction of the synthetic projection data may begin as soon as the first partial projection has been recorded. Once the complete virtual projection data is synthesized from the truncated partial projections, an image of the investigated object may be reconstructed using the wedge beam reconstruction method.

The above-described circular and linear methods horizontally extend the detector range of a cone beam scanner. An extension of the vertical detector limits in a similar fashion (synthesizing virtual projection data) is not desirable, since it would increase the vertical spread angle of the virtual projection. Thus, for an extension of the vertical detector limits in 3D CT, the above-described methods are repeated for various vertical object displacements specified by formulas set forth hereinafter (i.e., formulas (28) and (29) for both the linear cone beam synthetic scanner arrays and the circular cone beam synthetic scanner arrays), yielding image "cylinders" which are horizontally complete but vertically truncated. Stacking these image cylinders results in the final complete image of the investigated object.

For both of the above-described preferred methods, vertical extension of the detector limits requires an additional mechanical linear axis (i.e., the Z-axis) to vertically displace the turntable carrying the object.

FIGS. 5 and 16 illustrate the impact of circular and linear cone beam synthetic scanner arrays, respectively, on the reconstruction of a simulated object. Here, the detector limits are successively extended until the virtual detector covers the entire object and thus yields an artifact-free image.

The method of the present invention allows artifact-free reconstruction of objects significantly larger than the detector employed in the 3D CT scanner. In material science this method allows investigation of large samples as a whole and evaluation of the overall internal structure, stress response, etc. of composite materials or complex profiles. In quality assurance this method provides a tool for controlling and supervision of manufacturing processes involving large objects. Such objects include large automotive parts in general, awkwardly shaped specimen, parts of airplane wings, etc. Moreover, the method of the present invention can also be used in medical imaging and can be adapted for use in techniques such as ultrasonic inspection, diffractive tomography, impedance tomography, MRI scans, etc.

A summary of the development of the algorithms used in the method of the present invention is provided below. In Sections 1 and 2, two dimensional techniques are explained first as background material for the development of the method of the present invention, which is described in Sections 3 and 4.

SECTION 1

Background Material

The implementation of the projection scanner many times requires a departure from ideal conditions. An important limitation of the scanning hardware is the size of the detector: a small detector invariably causes spatial clipping when recording projections of objects extending over the detector boundaries. This results in characteristic truncation artifacts in the reconstructions, which seriously degrade the recovered images and prevents an accurate qualitative and quantitative object evaluation.

Figure 6:
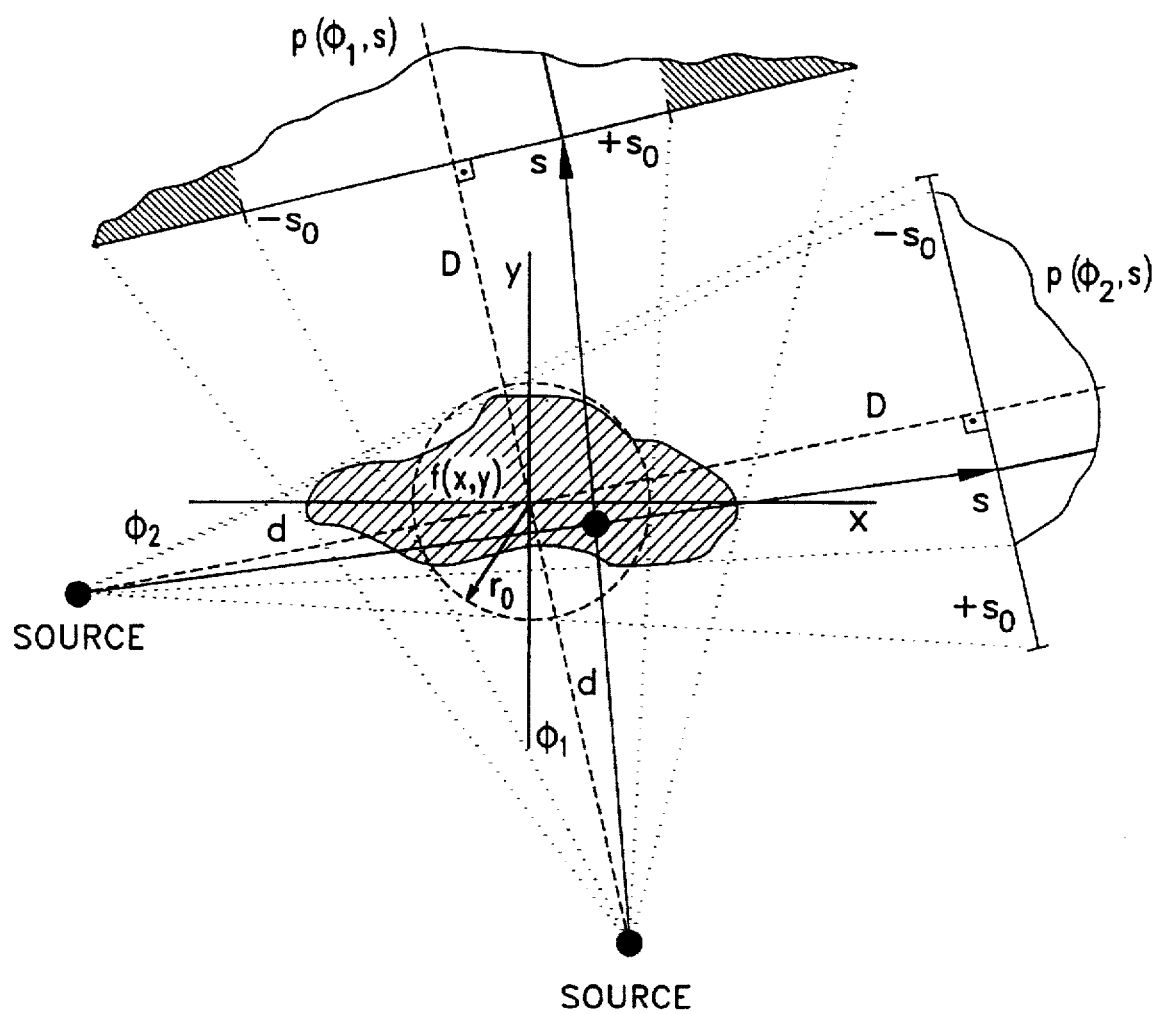
FIG. 6 shows a truncated fan beam projection. The detector has width $2s_0$. The projection at angle $\phi_2$ is complete, whereas the projection at angle $\phi_1$ is clipped, such that the shaded tails will not be included in $p(\phi_1, s)$. The dashed circle delimits the artifact-free zone of reconstruction. Objects inside this zone yield complete projections for all angles $0 \leq \phi \leq 2\pi$.

Referring to FIG. 6, at $\phi=\phi_1$ we have a truncated projection, while at $\phi=\phi_2$ the projection is complete. From FIG. 6, we evaluate the radius of the artifact-free zone as $$r_0 = \frac{s_0 d}{\sqrt{D^2 + s_0^2}} . \tag{1}$$

In M. Müller and G. R. Arce; "Truncation Artifacts in Tomographic Reconstructions from Projections", submitted to IEEE *Transactions on Image Processing*, 1993, we have analyzed the artifacts in reconstructions from truncated projections, where we provide a graphical scheme for prediction of the shape and location of the artifacts from the silhouette of the investigated object and the geometric parameters of the scanner. In the following paragraphs, we will discuss a method completely avoiding the distortions introduced by the reconstruction of objects from their truncated or clipped projections. Thus, the proposed method allows precise and artifact-free tomographic imaging of large objects, where the projections may be recorded with a small detector.

As we have shown in M. Müller and G. R. Arce; "Truncation Artifacts in Tomographic Reconstructions from Projections", submitted to IEEE *Transactions on Image Processing*, 1993, the artifacts due to truncated projections constitute serious limitations in tomographic systems, and their analytical description is important as are new methods to avoid these artifacts. Some reconstruction methods estimate the truncated portion of the projections using low-energy [see W. Wagner; "Reconstructions from Restricted Region Scan Data—New Means to Reduce the Patient Dose", IEEE *Transactions on Nuclear Science*, Vol. 26, 1979, pp. 2866–2869] and coarsely sampled [see O. Nalcioglu, Z. H. Chou, and R. Y. Lou; "Limited Field of View Reconstruction in Computerized Tomography", IEEE *Transactions on Nuclear Science*, Vol. 26, 1979, pp. 546–551] X-rays, or infrared light rays [W. Wagner; "Reconstructions from Restricted Region Scan Data—New Means to Reduce the Patient Dose", IEEE *Transactions on Nuclear Science*, Vol. 26, 1979, pp. 2866– 2869] to detect the outline of the object under investigation. Another approach is to employ linear prediction to recover the clipped tails of a projection from its statistics [see N. Srinivasa, V. Krishnan, K. R. Ramakrishnan, and K. Rajgopal; "Image Reconstruction from Truncated Projections: A Linear Prediction Approach", IEEE *Proceedings of the International Conference on Acoustics, Speech, and Signal Processing, Tokyo*, 1986; H. Stark; *Image Recovery—Theory and Application*, Academic Press, New York, 1987]. A thorough study of the limited angle (i.e., the projections angles do not extend over the full circle) problem is given in H. Stark; *Image Recovery—Theory and Application*, Academic Press, New York, 1987, while the following publications: G. T. Herman and R. M. Lewitt; "Evaluation of a Preprocessing Algorithm for Truncated CT Projections", *Journal of Computer Assisted Tomography*, Vol. 5, 1981, pp. 127–135; R. M. Lewitt and R. H. T. Bates; "Image Reconstruction from Projections" Parts I–IV, Optik, Wissenschaftliche Verlagsgesellschaft mbH Stuttgart, Vol. 50, 1978, pp. 19–33, 85–109, 189–204, 269–278; R. M. Lewitt;

"Processing of incomplete measurement data in computed tomography", *Medical Physics*, Vol. 6, 1979, pp. 412–417; S. H. Manglos; "Truncation artifact suppression in cone-beam radionuclide transmission CT using maximum likelihood techniques: evaluation with human subjects", *Physics in Medicine & Biology*, Vol. 37, 1992, pp. 549–562; F. Natterer; "The Mathematics of Computerized Tomography", *Teubner, Stuttgart, and Wiley*, New York, 1986; and K. Ogawa, M. Nakajima, and S. Yuta; "A Reconstruction Algorithm from Truncated Projections", *IEEE Transactions on Medical Imaging*, Vol 3, 1984, pp. 34–40, treat reconstructions from incomplete data in general. However, the methods proposed in the latter publications (i.e., G. T. Herman and R. M. Lewitt; "Evaluation of a Preprocessing Algorithm for Truncated CT Projections", *Journal of Computer Assisted Tomography*, Vol. 5, 1981, pp. 127–135; R. M. Lewitt and R. H. T. Bates; "Image Reconstruction from Projections" Parts I–IV, *Optik, Wissenschaftliche Verlagsgesellschaft mbH Stuttgart*, Vol. 50, 1978, pp. 19–33, 85–109, 189–204, 269–278; R. M. Lewitt; "Processing of incomplete measurement data in computed tomography", *Medical Physics*, Vol. 6, 1979, pp. 412–417; S. H. Manglos; "Truncation artifact suppression in cone-beam radionuclide transmission CT using maximum likelihood techniques: evaluation with human subjects", *Physics in Medicine & Biology*, Vol. 37, 1992, pp. 549–562; F. Natterer; "The Mathematics of Computerized Tomography", *Teubner, Stuttgart, and Wiley*, New York, 1986; and K. Ogawa, M. Nakajima, and S. Yuta; "A Reconstruction Algorithm from Truncated Projections", *IEEE Transactions on Medical Imaging*, Vol 3, 1984, pp. 34–40) improve the fidelity of the reconstructed images to a limited extend, and they are often concerned about a region of interest within the object under investigation. In D. Nahamoo, C. R. Crawford, and A. C. Kak; "Design Constraints and Reconstruction Algorithms for Traverse-Continuous-Rotate CT Scanners", *IEEE Transactions on Biomedical Engineering*, Vol. 28, 1981, pp. 79–98, the concepts of low-cost second and high-performance third-generation scanners are combined in a traverse-continuous-rotate scanner to find a compromise between cost and performance of scanning devices. Although the present method is based on a similar principle, we depart significantly from the approach in D. Nahamoo, C. R. Crawford, and A. C. Kak; "Design Constraints and Reconstruction Algorithms for Traverse-Continuous-Rotate CT Scanners", *IEEE Transactions on Biomedical Engineering*, Vol. 28, 1981, pp. 79–98, and obtain an efficient and easily implemented method to reconstruct accurate images from truncated sets of projections.

To date, there exist no methods that allow artifact-free reconstruction from truncated sets of projections, yielding accurate cone-beam 3-D reconstructions of the whole object. In G. L. Zeng and G. T. Gullberg; "A Study of Reconstruction Artifacts in Cone Beam Tomography using Filtered Backprojection and Iterative EM Algorithms", *IEEE Transactions on Nuclear Science*, Vol. 37, 1990, pp. 759–767, for instance, the importance of truncation artifacts is stressed, but neither is an analysis provided nor methods for accurate reconstruction from truncated projections are given. In the present method, we aim at a genuine representation of the whole object. We develop the mathematical framework for linear synthetic scanner arrays, which offer the simplest solution to the truncation problem for two-dimensional computerized tomography, but do not allow immediate extension to the three-dimensional case. Alternatively, we introduce the concept of circular synthetic scanner arrays, which are readily extended to a three-dimensional geometry.

The algorithm most widely used to reconstruct a three-dimensional object from cone beam projections is Feldkamp's cone beam convolution back projection algorithm introduced in 1984 [see L. A. Feldkamp, L. C. Davis, and J. W. Kress; "Practical cone beam algorithm", *Journal of the Optical Society of America*, Vol. 1, 1984, pp. 612–619]. Thus, we extend the method of synthetic scanner arrays to three-dimensional cone beam projections. For linear scanner arrays, we propose an approximate method which performed reasonably close to the exact circular case. In addition, we discuss the extension of the vertical limits of the artifact-free zone for cone beam scanners. We assume noise-free data for the analysis and development of the proposed algorithms. Thus, we are concentrating on the geometric aspects of the data completion process necessary to obtain truncation artifact-free reconstructions.

SECTION 2

Synthetic Fan Beam Scanner Arrays

The impulse response of the tomographic reconstructor for incomplete data is space-variant and in general has the form of a 2-dimensional modulated sinc function. For a linear space-variant system, characterized by the impulse response $h(x, y; x_e, y_e)$, the output $\hat{f}(x,y)$ due to the input $f(x_e, y_e)$ is given by $$\hat{f}(x,y) = f(x_e, y_e) * h(x, y; x_e, y_e) \qquad (2)$$

where * denotes the 2-dimensional convolution operation. Equation (2) suggests an inverse filtering approach to restore the distorted reconstruction $\hat{f}(x,y)$ of object $f(x,y)$. However, the spectrum of the impulse response $h(x,y; x_e, y_e)$ of the tomographic system contains large regions of zeros at locations where we wish to restore the spectrum. Thus, the inverse deblurring function $h^{-1}(x,y; x_e, y_e)$ in general does not exist, and the wide range of zeros in the spectrum of $h(x, y; x_e, y_e)$ makes an approximation difficult to obtain. An approximate deconvolution approach may cancel some of the distortions in reconstructions from truncated sets of projections. However, it cannot yield accurate images, since a set of truncated projections is not uniquely related to a given object. Thus, the resulting images are still distorted and to some degree depend on the choice of the algorithm estimating the missing data. An artifact-free reconstruction can only be obtained through a complete (and thus undistorted) set of projections.

The approach described here uses a number of partial sets of projections by translating/rotating the entire physical source-detector arrangement, such that the partial sets of projections can be merged into a complete virtual set of projections prior to reconstruction. While the partial sets of projections may be truncated, the virtual set of projections will be complete and thus yield an artifact-free reconstruction. Note that instead of moving the source-detector arrangement, it is often easier to move the object such that the scanner can remain in a fixed position. Thus, the source-detector arrangement can remain stationary, avoiding misalignment problems between the source and the detector which can cause additional artifacts in the reconstructions.

To obtain the partial sets of projections, the physical source-detector arrangements are placed such that they form either a linear or a circular array of scanners. Note that in practice only one scanner is needed, since we repeatedly position the object and take a partial set of projections until the ensemble of partial sets of projections can be merged into a complete virtual set of projections. In the next two sections we will analyze the geometry involved in linear and circular scanner arrays, and we develop the theory to reconstruct from the partial sets of projections which these arrays produce. It will be shown that a virtual set of projections is obtained from partial sets of projections through resorting.

For an array of scanners with parallel beam geometry, the partial sets of projections are obtained by horizontally moving the source-detector arrangements in multiples of the detector width $2s_o$. Thus, a virtual artifact-free zone of radius $(2N+1)s_o$ is obtained from $M=2N+1$ partial sets of projections $p_k(\phi,s)$ with $k=-N, \ldots, 0, \ldots, +N$, where each partial set of projections $p_k(\phi,s)$ is taken with the scanner shifted horizontally by $\Delta_{s,x}=2ks_o$ (or, equivalently, the object shifted by $-\Delta_{s,x}$). The virtual set of projections is the superposition of all partial sets of projections.

As mentioned earlier, however, fan beam sources are the predominant choice for tomographic scanners; thus, we will concentrate on the development of such a technique for arrays of scanners with fan beam geometry. In passing, we should note that the proposed method of partial sets of projections combining transversal positioning of the scanner with the usual object rotation is essentially a hybrid approach applying the underlying principles of second-and third-generation scanners. Another hybrid method (which is presented in D. Nahamoo, C. R. Crawford, and A. C. Kak; "Design Constraints and Reconstruction Algorithms for Traverse-Continuous-Rotate CT Scanners" IEEE Transactions on Biomedical Engineering, Vol 28, 1981, pp 79–98) combines second- and third-generation scanners to a traverse-continuous-rotate scanner, where the scanner is continuously swept over to object range while the object itself is rotated. While the method yields complete scan data using a small detector, it requires the translational motion of the scanner to be precisely synchronized with the object rotation, which in practice may be difficult to implement.

SECTION 2.1

Linear Scanner Arrays

In a linear array of fan beam scanners, the scanners are arranged with a horizontal displacement, such that the partial sets of projections allow for resorting into a complete virtual set of projections. To do so, it has to be assured that for a virtual artifact-free zone of radius $\tilde{r}_o$ encompassing the object $f(x,y)$, the ray displacements $\tau$ generated by the array of scanners continuously range within $-\tilde{r}_o \leq \tau \leq +\tilde{r}_o$, as would be the case with a single large enough detector. Recall that the ray displacement $\tau$ denotes the distance between a ray and the origin, where in a scanner array this distance is always measured with respect to the global origin, i.e., the local origin of the center scanner. FIG. 7 illustrates the geometry involved in a linear array of fan beam scanners.

Figure 8:
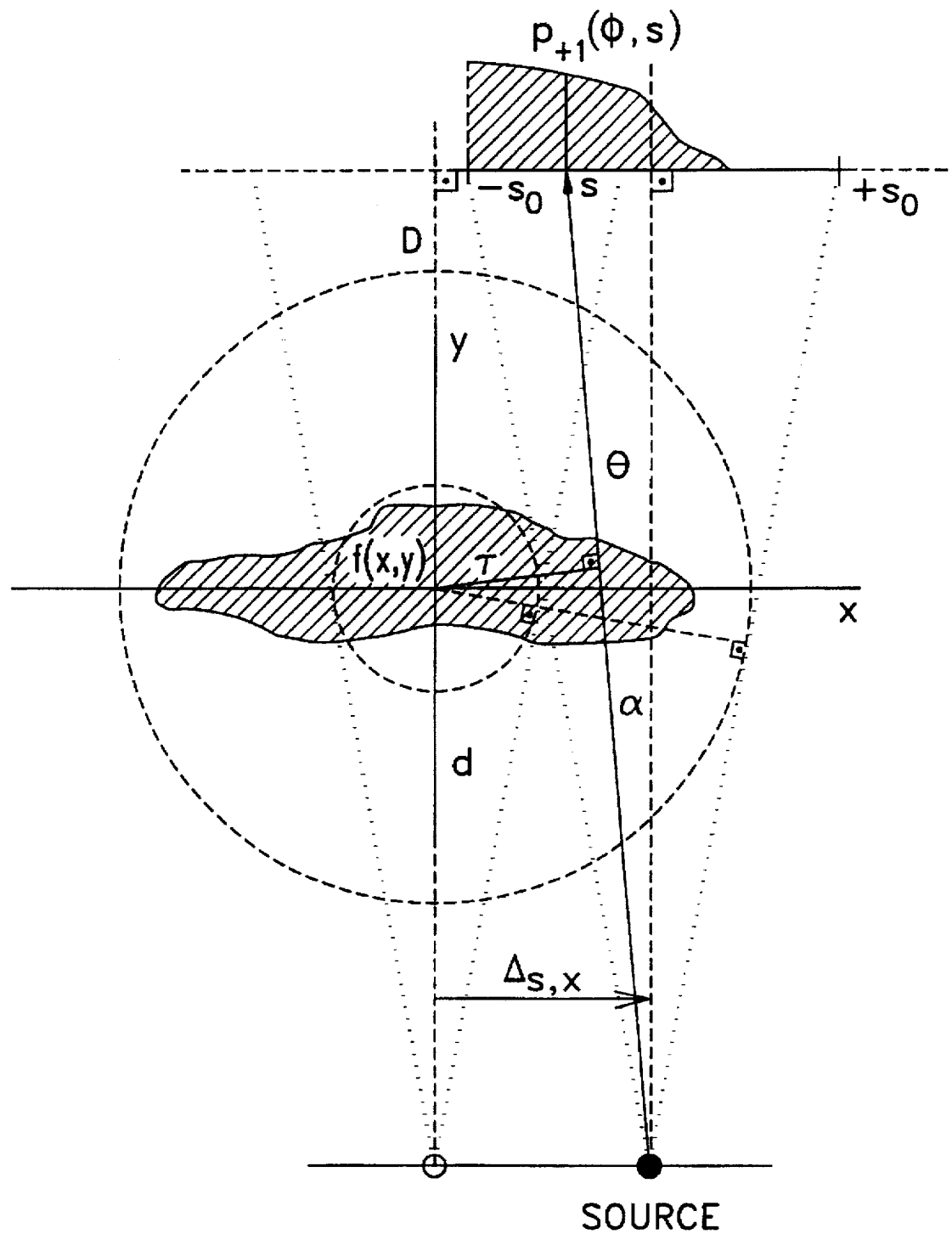
FIG. 8 shows the geometry that is used with linear arrays of fan beam scanners. The object is placed at position $\Delta x$. The parameter $\alpha$ denotes the relative beam angle, while $\theta$ and $\tau$ denote the ray angle and the ray displacement, respectively. The object is rotated around the origin of the (x,y) system.

The fan beam scanners with their detectors having width $2s_o$ are arranged such that a continuous range of ray displacements is covered, i.e., the maximum ray displacement obtained with an arbitrary scanner has to be equal to the minimum ray displacement yielded by its next adjacent scanner. This constraint on the horizontal displacements of the scanners results in some projection overlap. Each fan beam scanner is identical in its characteristic parameters D, d, and $s_o$, and is only distinguished by its horizontal displacement $\Delta_{s,x}$. Note that for clarity we equivalently use the variable $\Delta x_k = \Delta_{s,x}$ denoting the displacement $\Delta_{s,x}$ of the $k^{th}$ partial scanner for the remainder of this section. FIG. 8 further illustrates the geometry involved in linear arrays of fan beam scanners.

If the ray displacements are to cover a continuous range, then the maximum ray displacement yielded by a scanner shifted by $\Delta x_k$ must be equal to the minimum ray displacement yielded by its right adjacent scanner shifted by $\Delta x_{k+1}$. With the ray displacement $\tau=(sd+\Delta_{s,x}D)/\sqrt{D^2+s^2}$ as in Table 1, it can be shown that the ray displacement of an arbitrary scanner ranges in $\tau_{min} \leq \tau \leq \tau_{max}$, where $\tau_{min}=(-s_od+\Delta_{s,x}D)/\sqrt{D^2+s_o^2}$, and $\tau_{max}=(+s_od+\Delta_{s,x}D)/\sqrt{D^2+s_o^2}$ for all $\tau_{max} \leq d$. With the above we get the condition on $\Delta x_k$ for adjacent scanners yielding sets of projections $p_k(\phi,s)$ and $p_{k+1}(\phi,s)$ as $\Delta x_{k+1}-\Delta x_k=2s_od/D$. For $k=0$ and $\Delta x_o=0$ we clearly get $\Delta x_1=2s_od/D$, such that through induction it is shown that $$\Delta_{s,x}=2ks_od/D \text{ for } k=-N, \ldots, 0, \ldots, +N. \qquad (3)$$

TABLE 1

| Ray Parameter | Parallel Beam | Fan Beam | Fan Beam w/Displacement |
|---|---|---|---|
| Ray Angle $\theta$ | $\phi$ | $\phi + \alpha$ | $\phi + \alpha$ |
| Ray Displacement $\tau$ | s | $-d \sin(\alpha)$ | $(sd/D + \Delta_{s,x}) \cos(\alpha)$ |

Table 1 shows the ray parameters for parallel beam geometry, fan beam geometry and fan beam geometry with scanner displacement $\Delta_{s,x}$. With Table 1, the overall maximum ray displacement in a virtual set of projections obtained through $M=2N+1$ scanners becomes $\tau_{Max}=(s_od+\Delta x_N D)/\sqrt{D^2+s_o^2}$. Here $\Delta x_N$ denotes the displacement of the $N^{th}$ partial scanner. Note that the overall maximum ray displacement $\tau_{Max}$ is equivalent to the radius of the virtual artifact-free zone. With equation (3), the radius of the artifact-free zone becomes $\tilde{r}_o=(2N+1)r_o$, where $r_o=s_od/\sqrt{D^2+s_o^2}$ denotes the radius of the artifact-free zone of a single fan beam scanner as in equation (1). From the above we now can easily derive an expression to determine the number $M=2N+1$ of partial sets of projections required to yield a desired virtual artifact-free zone of radius $\tilde{r}_o$, such that $$N = \left\lceil \frac{1}{2} \left( \tilde{r}_o \frac{\sqrt{D^2+s_o^2}}{s_od} - 1 \right) \right\rceil, \qquad (4)$$

where the symbol "$\lceil \ \rceil$" (hereinafter referred to as "half-brackets") means that the value of the number within the half-brackets is rounded up to the next largest integer (i.e., 2.2 would be rounded up to 3). Note that $N \geq 0$, and for $N=0$ we have the case where the physical detector is sufficiently large to yield complete projections. Recall that the radius of the virtual artifact-free zone is limited to $\tilde{r}_o < d$.

Resorting each of the partial set of projections $p_k(\phi, s)$ into a patch $\tilde{p}_k(\phi,\tilde{s})$ of the virtual set of projections $\tilde{p}(\phi,\tilde{s})$, we get with $M=2N+1$ partial sets of projections, $$\tilde{p}(\phi,\tilde{s}) = \sum_{k=-N}^{+N} \tilde{p}_k(\phi,\tilde{s}), \qquad (5)$$

where N is determined from the fan beam parameters d, D and $s_o$, and the radius $\tilde{r}_o$ of the virtual artifact-free zone required to encompass an arbitrary object $f(x,y)$, as in (4). We next develop the resorting to map the partial sets of projections into a virtual set of parallel beam projections, such that we can subsequently apply a reconstruction algorithm designed for parallel beam geometry.

According to the ray parameters for parallel beam geometry in Table 1, the virtual parallel beam projection at the virtual coordinate $\tilde{s}$ results from a ray with ray displacement $\tau=\tilde{s}$.

With (3) we find the ray displacements in the $k^{th}$ partial projection $p_k(\phi, s)$ ranging from $\tau_{min}=(2k-1)r_o$ through $\tau_{max}=(2k+1)r_o$, such that $$k = \left[ \frac{1}{2} \frac{\tilde{s}\sqrt{D^2+s_0^2}}{s_0 d} \right] \quad (6)$$

is the index of the partial set of projections $p_k(\phi,s)$ yielding the virtual parallel beam projection at $\tilde{s}$. Note that the symbol "[]" (hereinafter referred to as brackets) means that the value of the number within the brackets is rounded to the nearest integer (i.e., 2.4 would be rounded to 2 and 2.6 would be rounded to 3). With the ray displacements in the $k^{th}$ partial set of projections $p_k(\phi,s)$ and the virtual set of parallel beam projections $\tilde{p}(\phi,\tilde{s})$ related through Table 1 as in $\tilde{s}=(sd+\Delta_{s,x}D)/\sqrt{D^2+s^2}$, it can be shown that the resorting is described as $$\tilde{p}_k(\phi,\tilde{s}) = p_k\left( \phi + \arctan\left(\frac{s}{D}\right), s \right) \quad (7)$$

$$s = \frac{2ks_0d^2 + \tilde{s}\sqrt{4k^2s_0^2d^2 + D^2(d^2-\tilde{s}^2)}}{d^2-\tilde{s}^2} \quad (8)$$

where $\tilde{p}_k(\phi,\tilde{s})$ is the $k^{th}$ patch of the virtual set of parallel beam projections as in $$\tilde{p}(\phi,\tilde{s}) = \sum_{k=-N}^{+N} \tilde{p}_k(\phi,\tilde{s}).$$

SECTION 2.2

Circular Scanner Arrays

With circular scanner arrays, the scanners are arranged in such a way, that the source always remains in a fixed position. We will show that the slightly more complicated geometry in circular scanner arrays yields a much simpler mapping. FIG. 9 illustrates the geometry involved in taking partial sets of projections with a circular array of fan beam scanners. As shown in FIG. 9, the physical detectors having width $2s_o$ are arranged such that they form a dome of radius D around the source. Note that each fan beam scanner is identical in its characteristic fan beam parameters D, d, and $s_o$, and is only distinguished by its tilt angle. An arbitrary projection $\tilde{p}(\phi,\tilde{s})$ onto the virtual detector is found through extrapolating a ray hitting a given physical detector patch to the virtual detector, i.e., relating the virtual detector coordinate $\tilde{s}$ to the physical detector measure s for a given physical detector patch.

Figure 10:
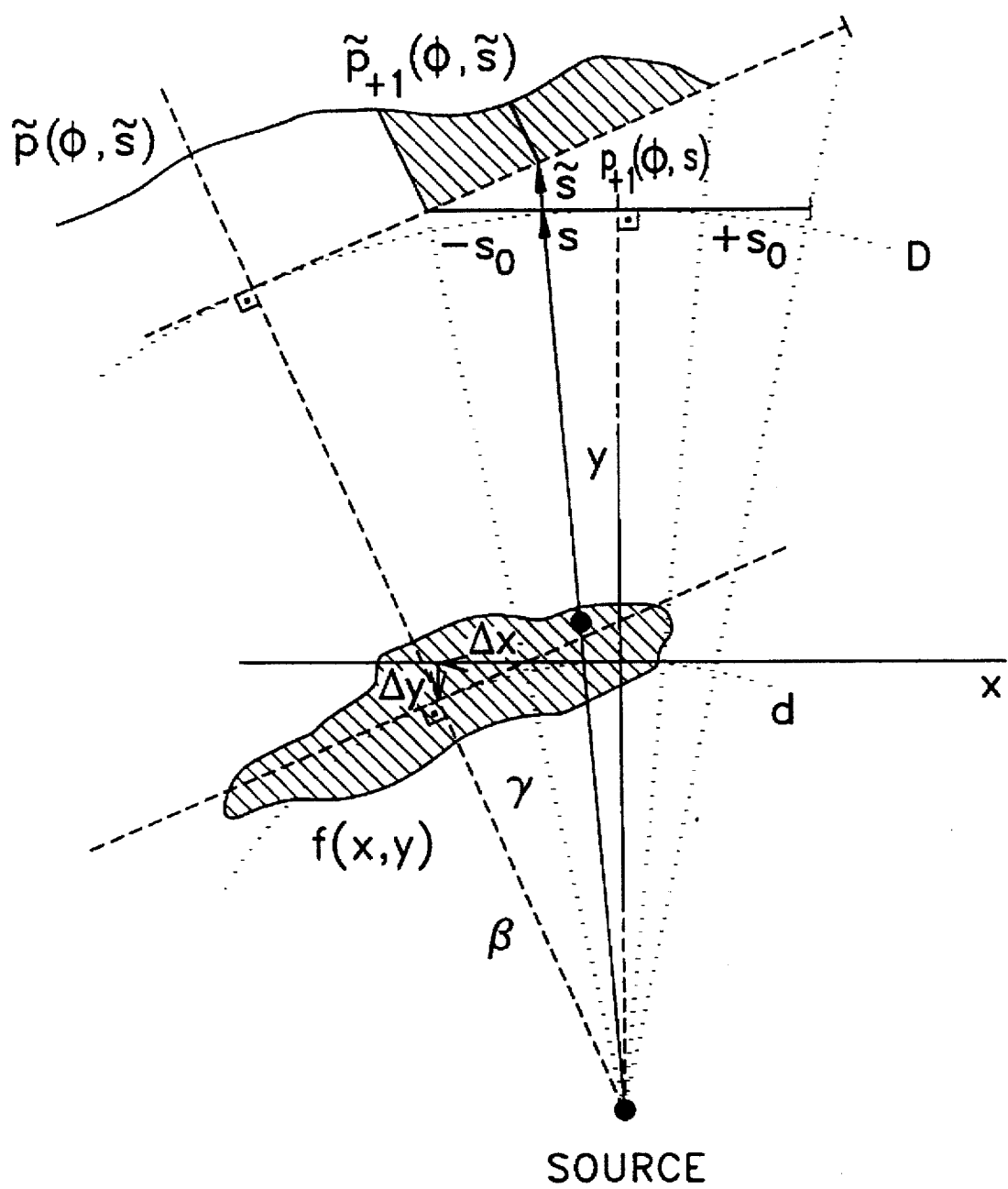
FIG. 10 shows a partial projection in a circular scanner array. The object is placed at position $(\Delta x, \Delta y)$ and pre-rotated by angle $\beta$. The physical partial projection $p_{+1}(\phi,s)$ of object f(x,y) is mapped into virtual partial projection $\tilde{p}_{+1}(\phi,\tilde{s})$ as a patch of the virtual projection $\tilde{p}(\phi,\tilde{s})$. Parameter $\gamma$ denotes the single-sided fan spread angle.
Figure 11A:
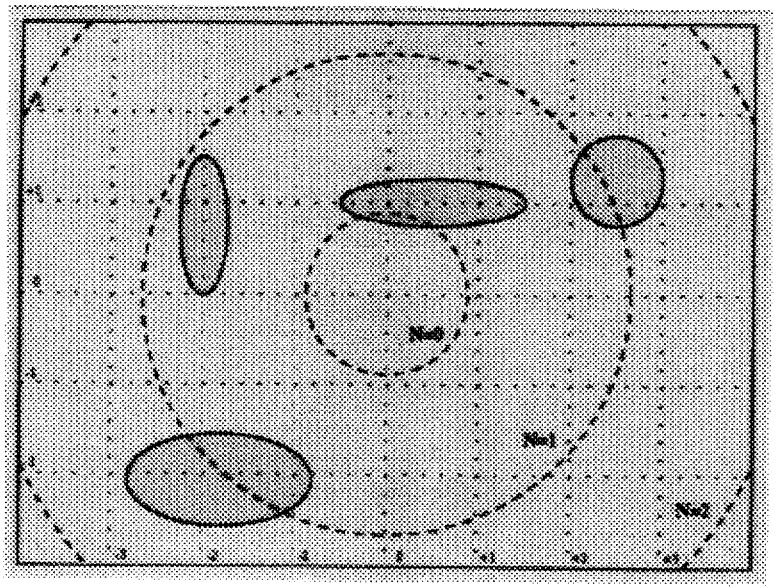
FIGS. 11A–D show reconstructions from virtual sets of parallel beam projections obtained with a linear fan beam scanner array. The partial sets of fan beam projections have been resorted before reconstruction. The parameters for the fan beam scanners are D=10.0, d=5.0, and $s_o$=1.8. The images have been enhanced through histogram modification.
Figure 11B:
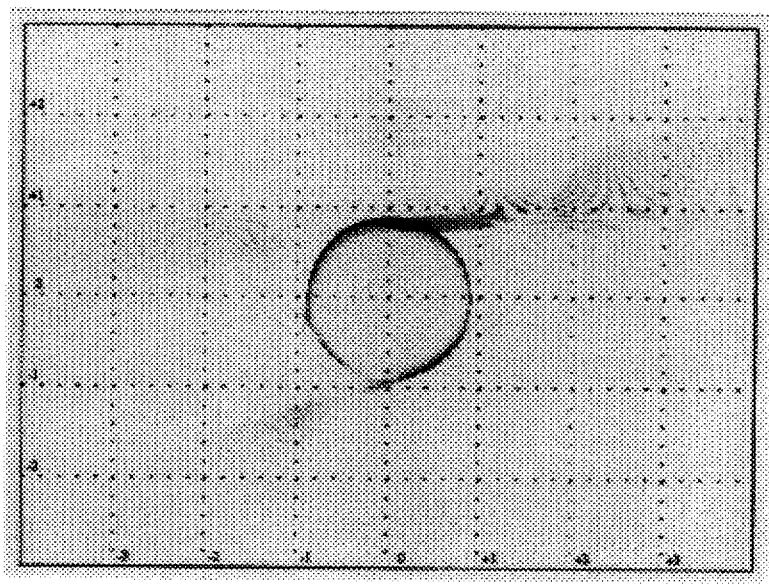
Figure 11C:
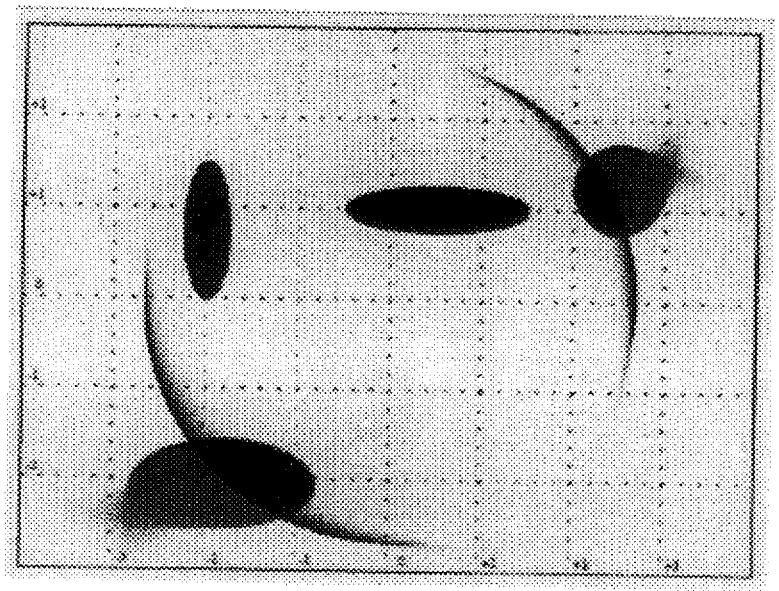
Figure 11D:
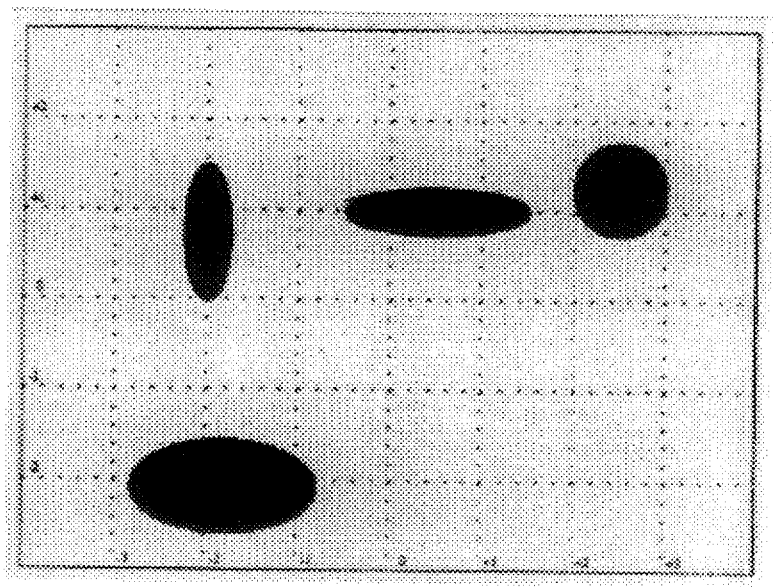

From FIG. 9 illustrating the extrapolation of $p_{+1}(\phi,s)$ to $\tilde{p}_{+1}(\phi,\tilde{s})$ it is easy to show that the displacement and the pre-rotation of the detector with respect to its normal position for the $k^{th}$ partial set of projections $p_k(\phi,s)$ becomes $$\Delta_{d,x}=D\sin(2k\gamma) \quad (9)$$

$$\Delta_{d,y}=D\cos(2k\gamma)-d \quad (10)$$

$$\psi_d=2k\gamma, \quad (11)$$

where $\Delta_{d,x}$, $\Delta_{d,y}$, and $\psi_d$ denote the detector displacements and detector tilt, respectively, as illustrated in FIG. 9. Note that the vertical detector displacement is measured with respect to the origin, such that for k=0, for instance, we have $\Delta_{d,y}=D-d$, as expected. In the above equations we have set $\gamma=\arctan(s_o/D)$ for $k=-N,\ldots,0,\ldots,+N$. Note also that the detector positioning in equations (9), (10), and (11) is equivalent to a more practical object placement $\Delta x=-d\sin(2k\gamma)$ and $\Delta y=d(\cos(2k\gamma)-1)$ with the object pre-rotated by $\beta=2k\gamma$, as shown in FIG. 10. Each scanner fan spans angle $2\gamma$, such that merging M=2N+1 partial sets of projections $p_k(\phi,s)$ with $k=-N,\ldots,0,\ldots,+N$ yields a virtual detector of size $\tilde{s}_o=D\tan((2N+1)\gamma)$. With equation (1) relating the radius of the artifact-free zone to the characteristic fan beam parameters D, d and $s_o$, we get $$N = \left[ \frac{1}{2}\left( \frac{\arcsin\left(\frac{\tilde{r}_o}{d}\right)}{\gamma} - 1 \right) \right], \quad (12)$$

where $\tilde{r}_o$ denotes the radius of the virtual artifact-free zone. Note that $N \geq 0$, and for N=0 we have the case where the physical detector is sufficiently large to yield complete projections. Recall that the radius of the virtual artifact-free zone is limited to $\tilde{r}_o < d$. With the virtual relative beam angle $\alpha=-\arctan(\tilde{s}/D)$ and the center beam for the kth physical detector patch having the virtual relative beam angle $\alpha_c=-2k\gamma$, we find $$k = \left[ \frac{\arctan\left(\frac{\tilde{s}}{D}\right)}{2\gamma} \right] \quad (13)$$

as the index of the partial set of projections $p_k(\phi,s)$ yielding the virtual projection at $\tilde{s}$. Note that the virtual relative beam angle $\alpha$ is measured with respect to the global vertical axis, i.e., the center beam of the center scanner. With (13), the virtual relative beam angles in the $k^{th}$ physical detector patch are found as $\alpha=-\arctan(s/D)-2k\gamma$. The coordinates s and $\tilde{s}$ in FIGS. 9 and 10 are related in that they denote the coordinates where a ray intersects the physical and virtual detector, respectively. In fact, they yield the same virtual relative beam angle, such that $\arctan(\tilde{s}/D)=\arctan(s/D)+2k\gamma$. This yields the mapping $$\tilde{p}_k(\phi,\tilde{s}) = p_k\left( \phi, D\frac{\tilde{s}-D\tan(2k\gamma)}{D+\tilde{s}\tan(2k\gamma)} \right), \quad (14)$$

where the above equation relates the coordinate $\tilde{s}$ on the virtual detector to the coordinate s on the $k^{th}$ physical detector patch. Note that for k=0 the above equation simplifies to $\tilde{p}_o(\phi,\tilde{s})=p_o(\phi,\tilde{s})$. Since we pre-rotate the detector by $\psi_d$ (or equivalently, the object by $\beta$), no resorting in $\phi$ is required.

Equations (13) and (14) map the partial sets of projections as in $p_k(\phi,s)$ into patches $\tilde{p}_k(\phi,\tilde{s})$ of the virtual set of projections. The complete virtual set of projections is then obtained through cumulatively summing the patches. Note that for a virtual relative beam angle $\alpha$ approaching $\pm\pi/2$, the limits of the virtual detector $\tilde{s}_o$ eventually become infinitely large. This occurs if in (12) the radius $\tilde{r}_o$ of the virtual artifact-free zone approaches d, such that the projections on the ±Nth physical detector are valid only up to the new upper and lower limit $s_o=\pm D\tan(\pi/2-2N\gamma)$ for the +Nth and −Nth detector, respectively.

FIG. 11 illustrates reconstructions from virtual sets of projections obtained with a scanner array. For a virtual artifact-free zone of radius $\sqrt{\tilde{r}_o} < d$, the virtual sets of projections obtained with linear and circular scanner arrays are identical. The linear scanner array, however, is better suited for a practical implementation with one detector, since the object is shifted in a straight line. FIG. 11 depicts the reconstructions from virtual sets of parallel beam projections resorted from partial sets of fan beam projections obtained with a linear scanner array, as described in the earlier section entitled "Linear Scanner Arrays" (i.e., Section 2.1). As illustrated in FIGS. 11B and 11C, the reconstructions from virtual sets of projections exhibit the same truncation artifacts as can be observed in reconstructions from projections obtained with single detectors. In fact, the virtual set of projections is indistinguishable from an equivalent set of projections obtained with a single physical detector.

SECTION 3

Synthetic Cone Beam Scanner Arrays

In this section, we extend the methods developed for the two-dimensional case to three-dimensional cone beam geometry. Thus, we next develop the extent of the artifact-free zone due to cone beam projections, and subsequently extend its radius by applying the concept of synthetic scanner arrays. While the radius of the artifact-free zone of reconstruction from cone beam projections remains $r_o = s_o d/\sqrt{D^2 + s_o^2}$ as for parallel fan beam projection planes, the top and bottom facets of the cylindric artifact-free zone in cone beam geometry are cones rather than planes due to the tilted projection planes, as depicted in FIG. 12B.

Figure 12A:
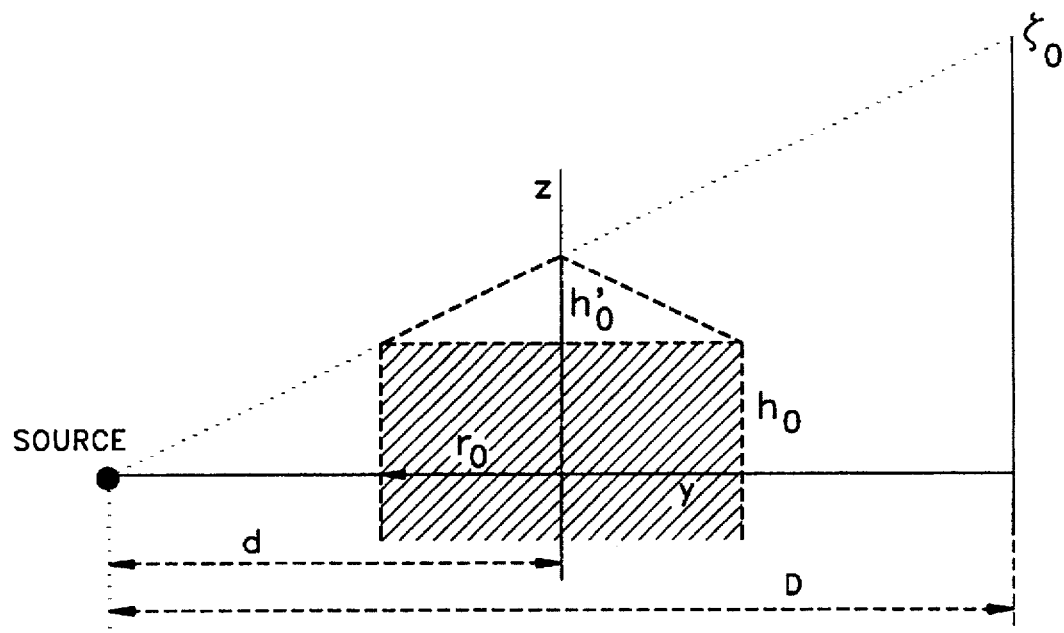
FIGS. 12(A) and (B) show the artifact-free zone of reconstruction for quasi three-dimensional cone beam projections. Parameter $r_o$ denotes the radius of the cylindric artifact-free zone, while $h_o$ and $h'_o$ denote the height of the cylinder and the elevation of its conical facets, respectively. The shaded regions depict the cylindrical portion of the artifact-free zone.
Figure 12B:
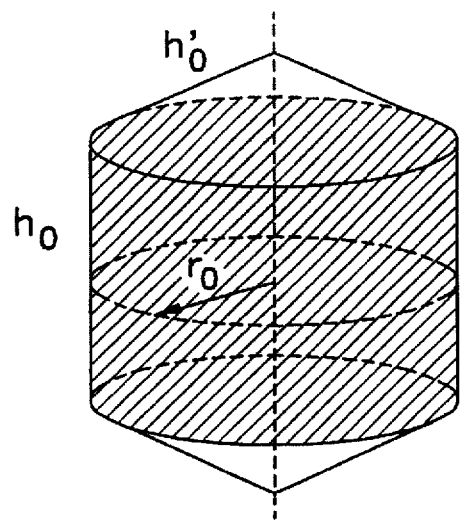
FIG. 12(B) shows the volume of the three-dimensional artifact-free zone of reconstruction.

FIG. 12A illustrates the geometry of the artifact-free zone of reconstruction for quasi three-dimensional cone beam projections. From FIG. 12A follows $$r_0 = \frac{s_0 d}{\sqrt{D^2 + s_0^2}} \quad (15)$$

$$h_0 = \zeta_0 \frac{d - r_0}{D} \quad (16)$$

$$h'_0 = \zeta_0 \frac{r_0}{D} . \quad (17)$$

Parameters $r_o$, $h_o$ and $h'_o$ denote the cylinder radius, height, and the cone elevation, respectively.

The shape of the artifact-free zone of reconstruction for quasi three-dimensional cone beam projections is depicted in FIG. 12B.

We will first be concerned with extending the radius of the artifact-free zone, and subsequently provide the extension in the vertical dimension. In Section 2 we have shown that complete virtual scan data can be obtained from an ensemble of truncated partial scans if the ray displacements generated by the array of scanners continuously range within $\tilde{r}_o \leq \tilde{\tau} \leq +\tilde{r}_o$, where $\tilde{r}_o$ denotes the radius of the virtual artifact-free zone.

Figure 13:
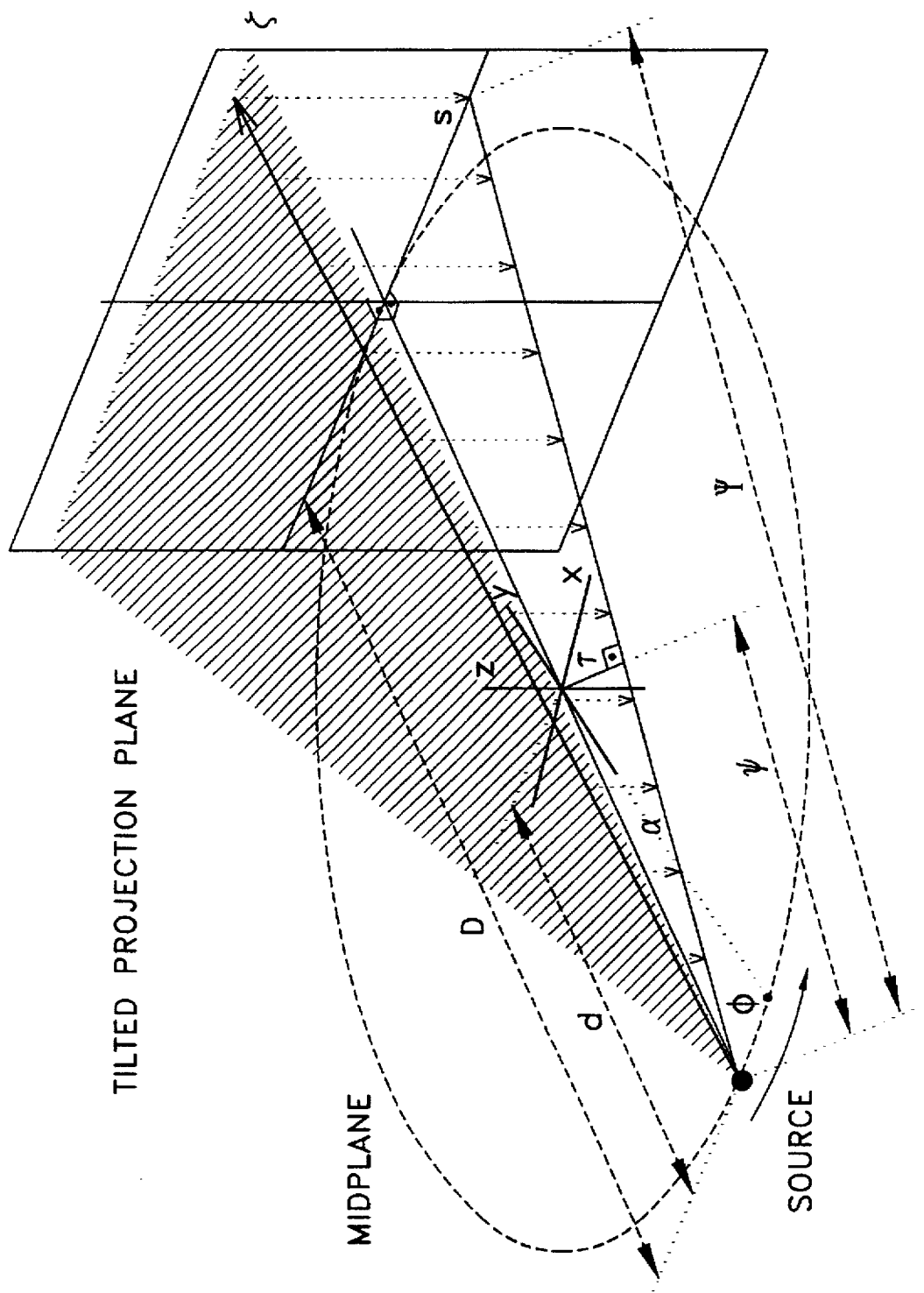
FIG. 13 shows the ray parameters for three-dimensional cone beam geometry. Parameters D and d denote the source-to-detector and source-to-object distance, respectively. Parameter $\phi$ denotes the projection angle, while $\alpha$ denotes the relative beam angle. Parameters $\tau$, and $\Psi$ and $\psi$ denote the ray displacement, and the projected ray source-to-detector and source-to-object distance, respectively.

From FIG. 13 we define a number of new cone beam parameters. Parameters D and d denoting the source-to-detector and source-to-object distances and $\phi$ denoting the projection angle are retained from two-dimensional fan beam geometry as is the horizontal detector coordinate s. The parameters $\alpha$ and $\tau$, however, are now obtained by projecting an arbitrary ray onto the mid-plane and deriving its relative ray angle and ray displacement. For two-dimensional detector planes we use $\zeta$ denoting the vertical detector coordinate. In addition, we introduce the mid-plane parameters $\Psi$ and $\psi$ denoting the projected ray source-to-detector and source-to-object distances. Note that for the scanner depicted in FIG. 13, we have $d^2 = \psi^2 + \tau^2$. While parameters $\Psi$ and $\psi$ are of little significance in two-dimensional fan beam geometry, they play an important role in three-dimensional cone beam geometry, and we will make extensive use of these parameters in Section 3.2. We first consider the method of circular synthetic scanner arrays, and subsequently treat the alternative method of linear synthetic scanner arrays.

Figure 14E:
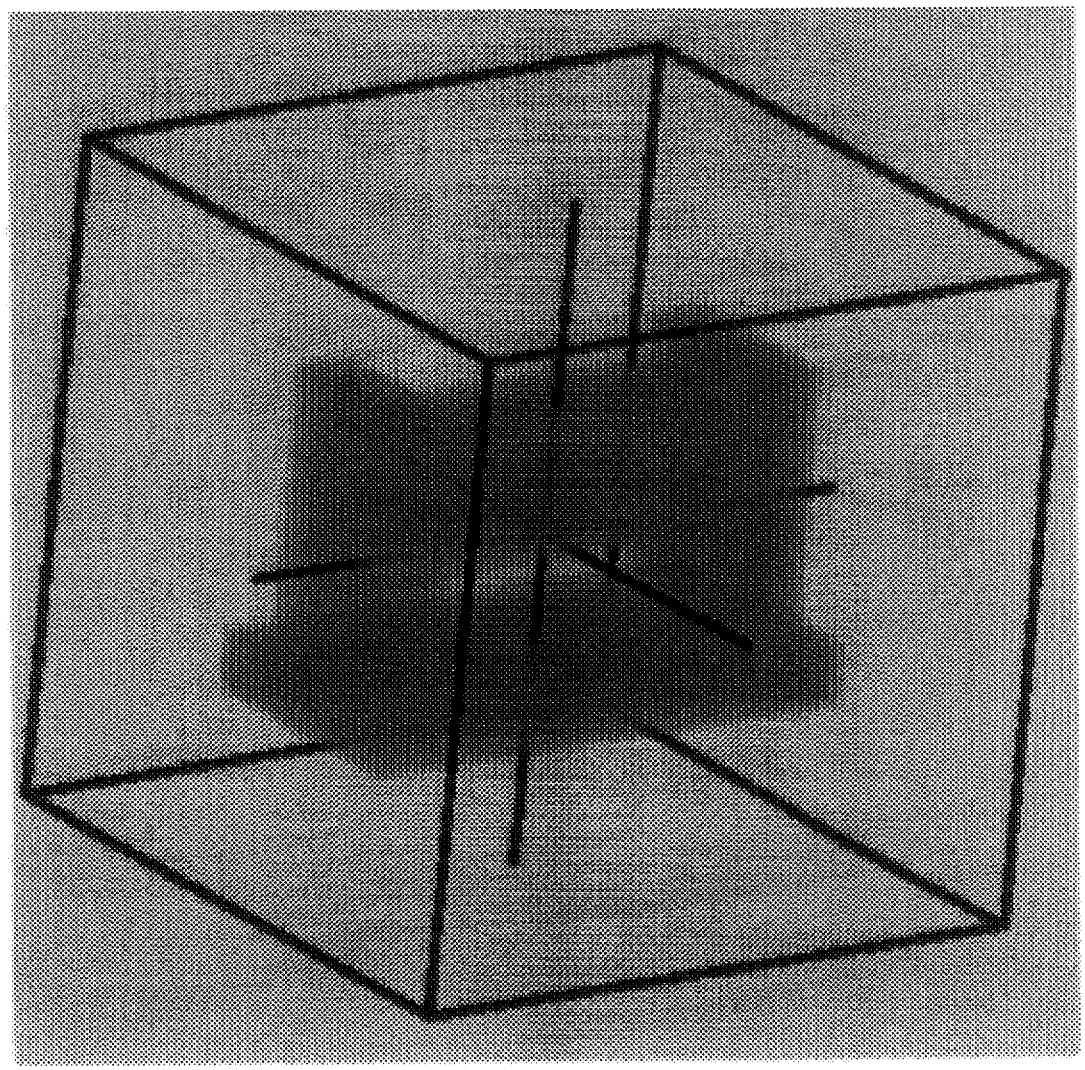
FIG. 14(E) shows a volumetric image of the simulated object of FIG. 14(A).

We evaluate the performance of the developed resorting algorithms by reconstructing the object shown in FIG. 14 from its simulated projections. Note that all reconstructions are computed without smoothing to emphasize the raw image performance of the studied algorithms. Smoothing, e.g., application of a raised-cosine filter of Hamming/Hanning window in the frequency domain during reconstruction, substantially reduces the presence of aliasing artifacts and thus improves the image quality. Unless otherwise noted, the projections are of resolution $N_\phi \times N_\zeta \times N_s = 101 \times 101 \times 101$, with $N_\phi$ the number of projections, while $N_\zeta$ and $N_s$ denote the number of vertical and horizontal samples per projection, respectively. All reconstructed images are compared with a reconstruction from ideal three-dimensional fan beam data obtained with a two-dimensional fan beam scanner swept over the vertical range of the simulated cone beam detector. As a quantitative measure of the distance between the compared images, we provide rms-error values. In addition, we provide correlation coefficients as a qualitative measure of the visual similarity between two images.

SECTION 3.1

Circular Scanner Arrays

Figure 3:
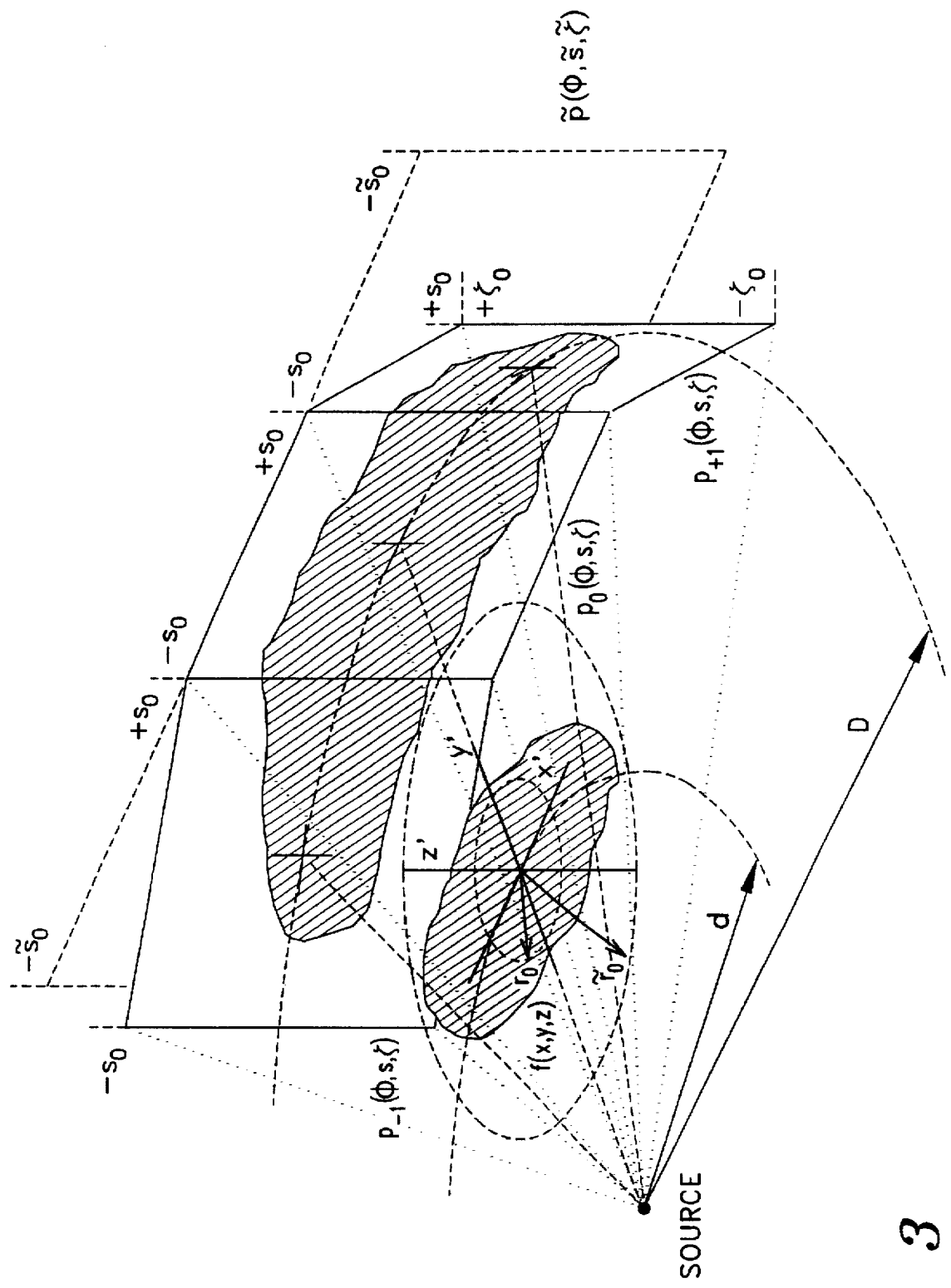
FIG. 3 shows a circular cone beam scanner array. Parameters D and d denote the source-to-detector and source-to-object distances, respectively, while $\pm s_o$ and $\pm \zeta_o$ denote the detector size. Parameter $r_o$ denotes the radius of the artifact-free zone for the center cone beam scanner, while $\tilde{r}_0$ denotes the radius of the virtual artifact-free zone due to the combination of three partial cone beam scanners.

FIG. 3 illustrates the extension of the circular scanner array to three-dimensional cone beam geometry. In a circular cone beam scanner array we have the additional vertical detector coordinate $\zeta$, which requires an extension of the two-dimensional fan beam mapping revisited above.

The mapping of the vertical detector coordinate $\zeta$ for the virtual set of cone beam projections and $\tilde\zeta$ for the partial sets of cone beam projections is straightforward, such that we immediately find $\zeta/\sqrt{D^2+s^2} = \tilde\zeta/\sqrt{D^2+\tilde s^2}$. We thus resort the partial cone beam scans as $$\tilde p_k(\phi,\tilde s,\tilde\zeta) = p_k\left(\phi, D\frac{\tilde s - D\tan(2k\gamma)}{D + \tilde s\tan(2k\gamma)}, \tilde\zeta\sqrt{\frac{D^2+\tilde s^2}{D^2+s^2}}\right) \quad (18)$$

where the complete virtual set of cone beam projections is found as $$\tilde p(\phi,\tilde s,\tilde\zeta) = \sum_{k=-N}^{+N} \tilde p_k(\phi,\tilde s,\tilde\zeta).$$

Equation (18) resorts an ensemble of partial sets of cone beam projections into a virtual set of cone beam projections, from which we subsequently reconstruct the investigated object with a standard cone beam reconstruction algorithm. For the partial sets of cone beam projections, the object is positioned identically to the two-dimensional fan beam case.

FIG. 6 depicts reconstructions from virtual scan data due to partial scan data in a circular synthetic cone beam scanner array. In FIG. 6B we reconstruct from data obtained with a single cone beam scanner such that due to a small artifact-free zone the object almost completely disintegrates into truncation artifacts, and we clearly see the cylindrical limits of the artifact-free zone. In FIG. 6C, on the other hand, the radius of the artifact-free zone has been extended using three partial scans, and the center portion of the object is reconstructed with fewer artifacts. In FIG. 6D, finally, using 5 partial cone beam scans the artifact-free zone is sufficiently large to completely encompass the object, such that no truncation artifacts remain in the reconstruction. See Table 2 and FIG. 17 for a comparative evaluation of the image performance of circular synthetic cone beam scanner arrays.

SECTION 3.2

Linear Scanner Arrays

We next consider the application of linear synthetic scanner arrays to cone beam geometry, as illustrated in FIG. 4.

As depicted in FIG. 13 for a linear cone beam scanner array, in three-dimensional cone beam geometry we are dealing with rays traveling through space (i.e., on tilted projection planes) rather than a single horizontal plane, such that we have defined the ray angle $\alpha$ and the ray displacement $\tau$ of a ray in three-dimensional geometry as the ray angle and the ray displacement of its two-dimensional projection onto the mid-plane (i.e., the XY plane). We also have defined the new mid-plane parameters $\Psi$ and $\psi$ as the individual ray source-to-detector and source-to-object distances projected onto the mid-plane. As easily seen from FIG. 13, we write $$\psi(s) = \sqrt{D^2 + s^2} \tag{19}$$

$$\psi(\Delta_{s,x}, s) = \frac{Dd - s\Delta_{s,x}}{\sqrt{D^2 + s^2}} \tag{20}$$

Figure 15B:
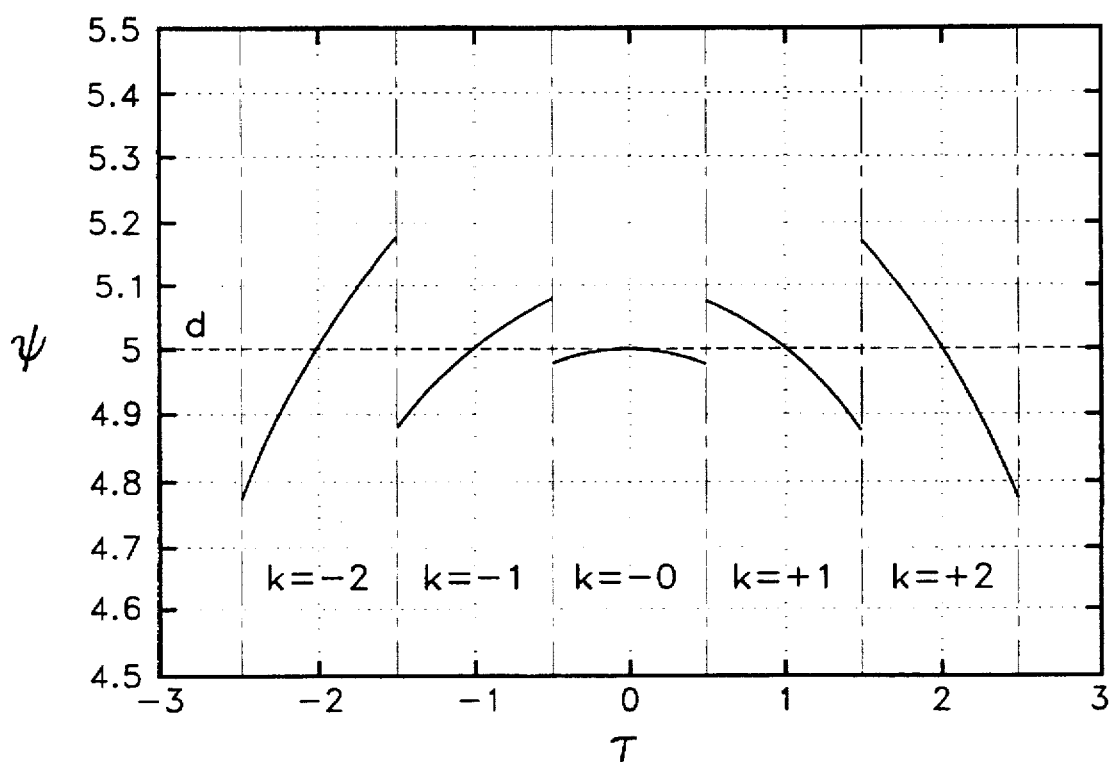
Figure 16A:
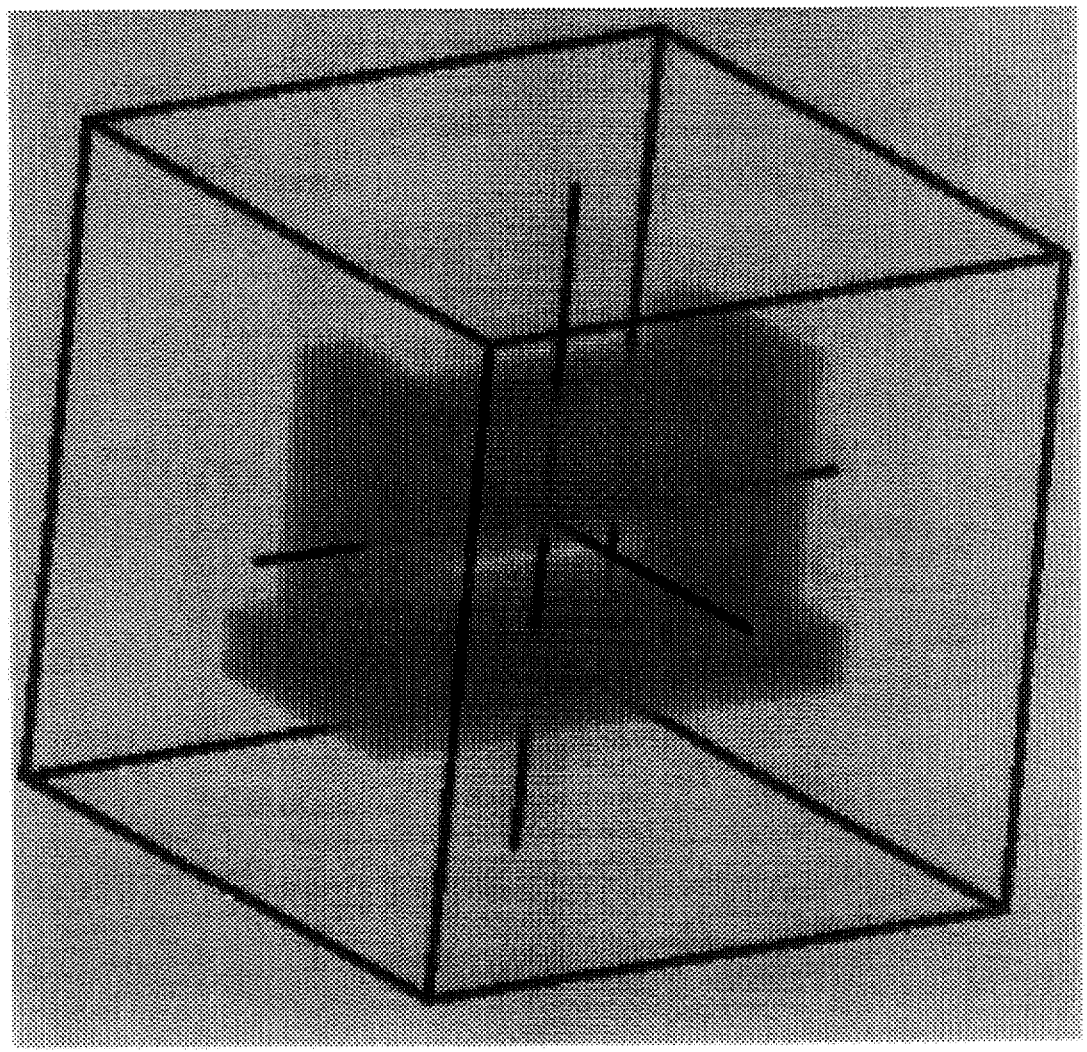
FIGS. 16A–D show the volumetric images of reconstructions from virtual sets of wedge beam projections, resorted from partial cone beam scans due to a linear synthetic scanner array. The bright regions in the images depict artifacts. Specifically.
Figure 16B:
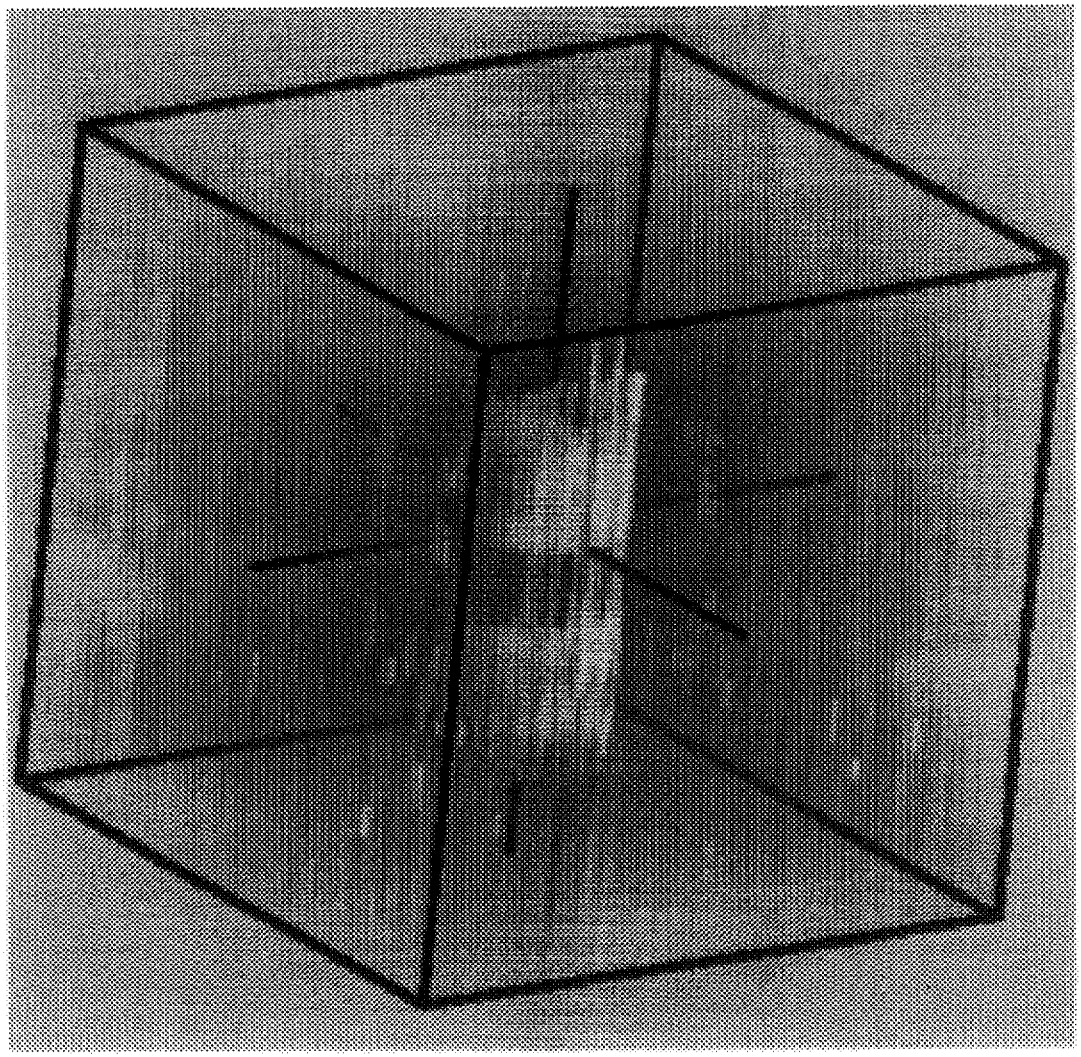
Figure 16C:
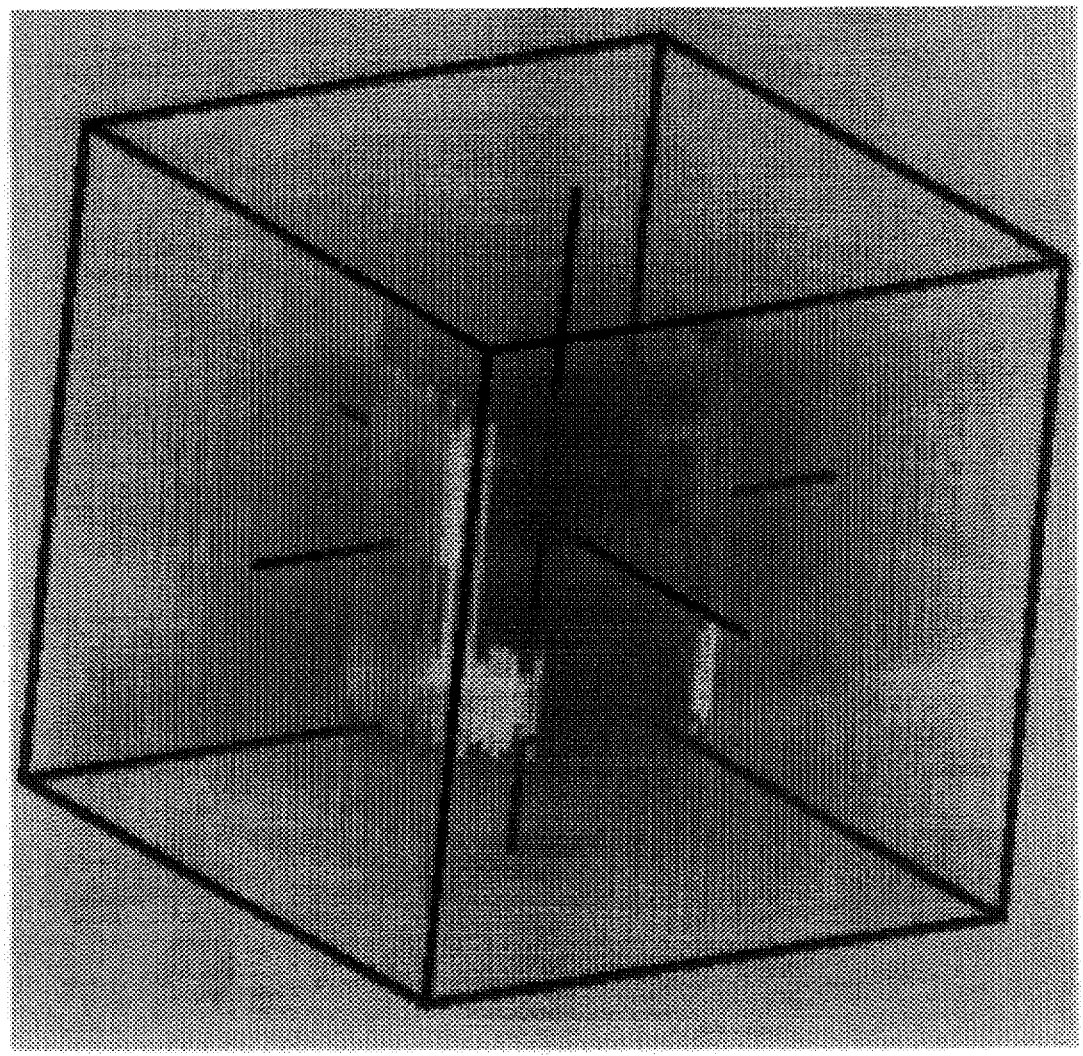
Figure 16D:
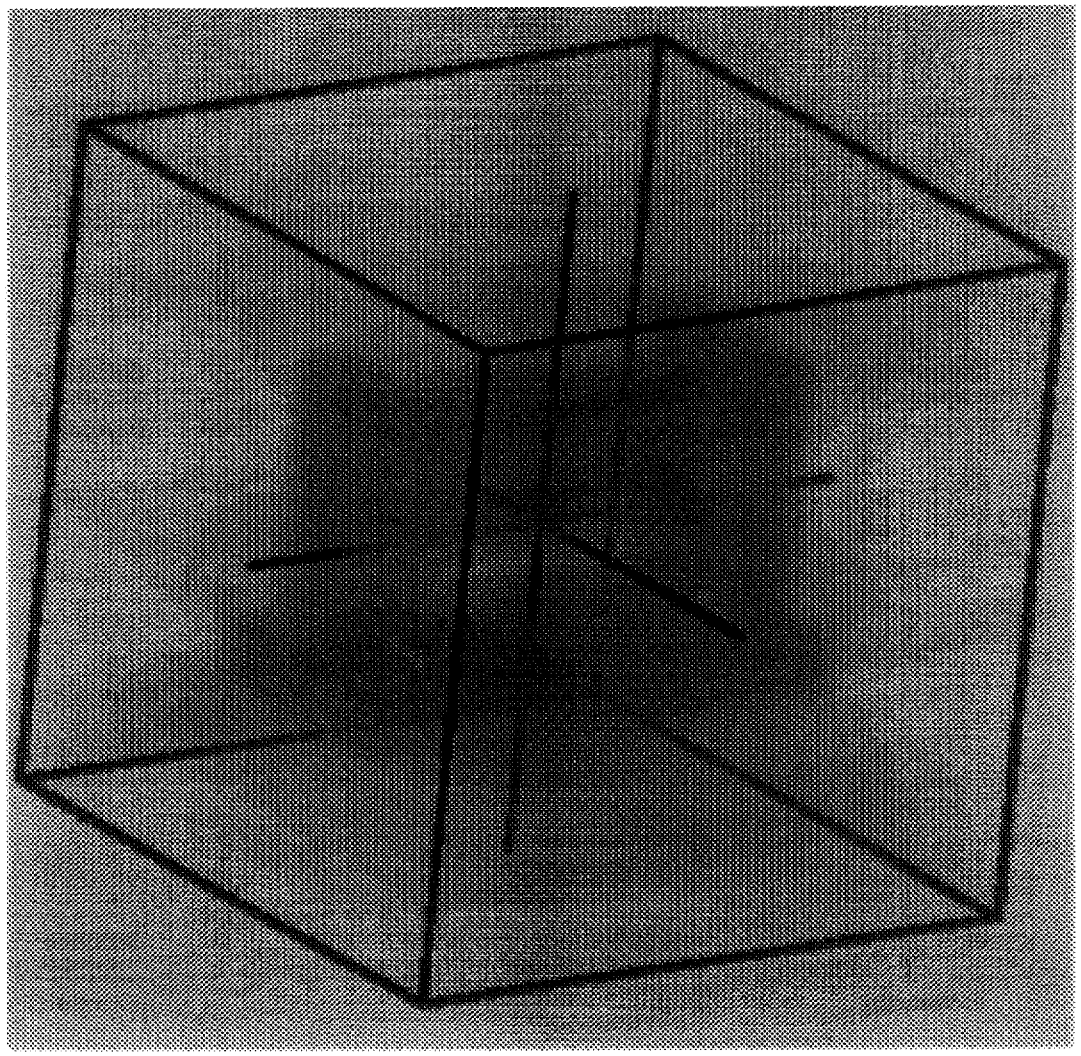

Since Feldkamp's cone beam algorithm requires a constant source-to-object distance d, an ensemble of partial sets of cone beam projections taken with a linear synthetic array cannot be resorted in a virtual complete set of cone beam projections. For a cone beam projection, we need $\psi(s) = Dd/\sqrt{D^2 + s^2}$. Therefore, equation (20) describes the introduction of source jitter, i.e., the resorted rays will not intersect the mid-plane at a single location and thus do not lead to a consistent source position. It can be shown that, due to the fact that the quasi three-dimensional cone beam geometry yields a severely constrained set of projections, a linear synthetic cone beam scanner array does not provide the sets of partial projections necessary for extension of the artifact-free zone. However, due to the mechanical simplicity of linear scanner arrays (i.e., only one additional linear axis is needed for their implementation), we continue with our analysis and develop an approximate method for resorting of partial sets of cone beam projections. Resorting the partial sets of cone beam projections $p_k(\phi, s, \zeta)$ into a set of wedge beam projections, we reconstruct $$f(x,y,z) = \int_0^\pi \int_{-\infty}^{+\infty} p(\phi,s,\zeta) h_w(x' - s) ds \, d\phi \tag{21}$$

with $x' = x \cos(\phi) + y \sin(\phi)$. Here we set $\zeta = zD/(y'+d)$ for an ideal wedge beam reconstruction, where we have constant projected distances $\Psi = D$ and $\psi = d$, as illustrated in FIG. 15A. However for partial sets of cone beam projections $\Psi(s)$ and $\psi(\Delta_{s,x}, s)$ are functions of the scanner displacement $\Delta_{s,x}$ and the detector coordinate s, such that the vertical detector coordinate becomes $$\zeta = \frac{z\sqrt{D^2 + s^2}}{y' + \psi}, \tag{22}$$

where $y' = y \cos(\phi) - x \sin(\phi)$ and as before we have set $z' = z$. FIG. 15B depicts the projected source-to-object distance $\psi$ as a function of the ray displacement $\tau = (sd + \Delta_{s,x} D)/\sqrt{D^2 + s^2}$ for an ensemble of 5 partial sets of cone beam projections.

To compensate for the source jitter introduced by $\psi(s)$, we resort the partial sets of cone beam projections into a virtual set of wedge beam projections, where we set the virtual vertical detector coordinate to $\zeta = \zeta \Psi/\sqrt{D^2 + s^2}$. Thus, for optimal compensation we set the virtual source-to-detector distance $$\tilde\Psi = \frac{D}{d}(y'_c + \psi) \tag{23}$$

with $y_c = y_c \cos(\phi) - x_c \sin(\phi)$, where $(x_c, y_c)^\tau$ denotes the center of continuous projection. From experimental results we recommend $(x_c, y_c)^\tau = 0$, since the center of mass in the investigated objects is usually aligned with the axis of rotation. With $\tilde\Psi$ in the above equation used in (22), we find the vertical virtual detector coordinate $$\tilde\zeta = \frac{zD}{d} \frac{y'_c + \psi}{y' + \psi}, \tag{24}$$

which for $y' = y'_c$ collapses to the ideal case $\zeta = zD/d$, where the source jitter introduced by $\psi$ cancels out. At projection angle $\phi$ all points on the X'Z plane (i.e., the XZ plane rotated by $\phi$) yield a continuous projection since $y' = y'_c$, as do all points $(x, y, 0)^\tau$ located on the XY plane. Projected points not located on these planes are subjected to the discontinuous source-to-detector distance $\psi$ as depicted in FIG. 15B and thus will result in a discontinuous projection image. With a proper choice for the center of continuous projection, however, the discontinuities in virtual scans due to linear synthetic cone beam scanner arrays are substantially reduced. Due to the band-limited filter function $h_w$ employed by the filtered convolution back projection reconstruction algorithm, discontinuities in the projection data inevitably cause ringing artifacts in the reconstruction. Note that for a set of projections taken over the full circle, the set of planes of continuous projection intersect at $(x_c, y_c)^\tau$, the center of continuous projection. Note also that from the wedge beam geometry depicted in FIG. 15A and from the fact that the source jitter only affects the vertical detector coordinate $\zeta$, we deduce that objects translationally symmetric with respect to the Z axis do not result in discontinuous projections. We summarize our analysis by presenting the mapping of an ensemble of partial cone beam projections into a virtual set of wedge beam projections. From the above analysis, we get $$\tilde p_k(\phi, \tilde s, \tilde\zeta) = p_k\left(\phi + \arctan\left(\frac{s}{D}\right), s, \zeta\right) \tag{25}$$

$$s = \frac{-2ks_0 d^2 + \tilde s\sqrt{4k^2 s_0^2 d^2 + D^2(d^2 - \tilde s^2)}}{d^2 - \tilde s^2} \tag{26}$$

$$\zeta = \tilde\zeta \frac{d\sqrt{D^2 + s^2}}{D(y'_c + \psi)} \tag{27}$$

with $y'$ and $y'_c$ as defined earlier. The complete virtual set of wedge beam projections is found as $$\tilde p(\phi, \tilde s, \tilde\zeta) = \sum_{k=-N}^{+N} \tilde p_k(\phi, \tilde s, \tilde\zeta).$$

For the partial sets of cone beam projections, the object is positioned identically to the two-dimensional fan beam case. The object is reconstructed from the virtual set of wedge beam projections generated from the above set of equations with the wedge beam convolution back projection algorithm introduced in (21), where we replace $\zeta$ by the virtual vertical detector coordinate $\tilde\zeta$ as defined in (24). FIG. 16 depicts reconstructions from virtual sets of wedge beam projections resorted from an ensemble of 5 partial sets of cone beam projections.

As shown in this section, the source jitter introduced by $\psi$ requires modification both of the resorting and reconstruction algorithms. While the back projection is easily adapted to the new geometry as shown in equation (24), the constrained sets of partial cone beam projections cannot be resorted into a virtual set of wedge beam projections (or any other geometry for that matter) without introducing discontinuities in the virtual projections.

Figure 17A:
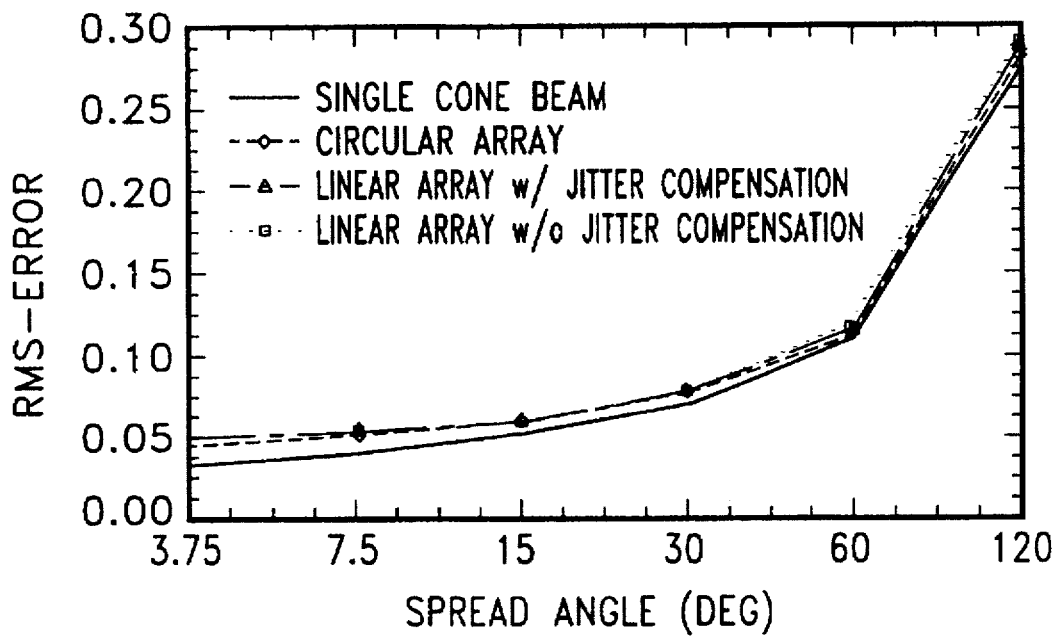
FIG. 17(A) shows rms-error in reconstructions from cone beam data and virtual scan data due to circular and linear synthetic scanner arrays for a range of spread angles.
Figure 17B:
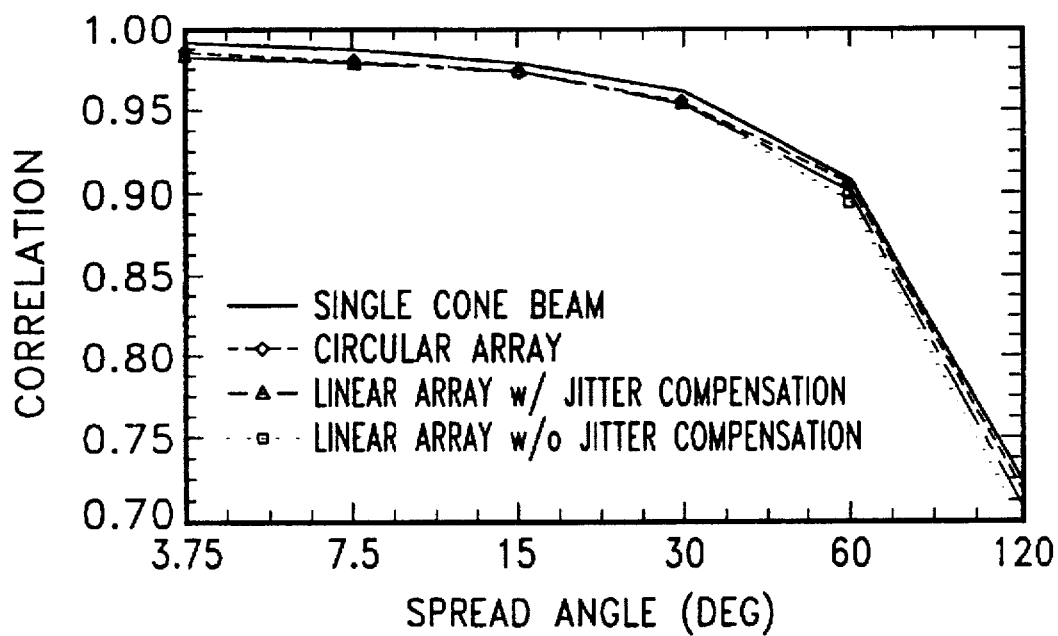
FIG. 17(B) shows correlation in reconstructions from cone beam data and virtual scan data due to circular and linear synthetic scanner arrays for a range of spread angles.

Thus, the band-limited filtering with $h_{wo}$ prior to back projection employed by the filtered back projection convolution reconstruction algorithm causes local artifacts at the discontinuities due to filter ringing. FIG. 17 and Table 2 provide a comparative evaluation of the performance of synthetic cone beam scanner arrays. The spread angle refers the horizontal and vertical cone beam spread for a single non-truncated scan with a square detector. The reconstructions due to synthetic scanner arrays are based on virtual scan data resorted from 5 partial scans, where the virtual artifact-free zones of an extent equal to the single cone beam case. For linear arrays without source jitter compensation we have set $\Psi=D$. All reconstructions are compared with wobble-free reconstructions from three-dimensional fan beam data.

As shown in FIG. 17 and Table 2, the performance of the synthetic scanner arrays is approaching that of a reconstruction from cone beam data obtained with a single large detector.

TABLE 2

| Spread Angle | 3.75 deg | 7.5 deg | 15 deg | 30 deg | 60 deg | 120 deg |
|---|---|---|---|---|---|---|
| | | | Single Cone Beam | | | |
| RMS-Error | 0.03285 | 0.04050 | 0.05169 | 0.07021 | 0.10827 | 0.27247 |
| Correlation | 0.99164 | 0.98728 | 0.97916 | 0.96157 | 0.90818 | 0.72378 |
| | | Circular Synthetic Cone Beam Array | | | | |
| RMS-Error | 0.04415 | 0.04961 | 0.05858 | 0.07579 | 0.11004 | 0.27504 |
| Correlation | 0.98488 | 0.98091 | 0.97321 | 0.95511 | 0.90519 | 0.71662 |
| | Linear Synthetic Cone Beam Array w/ Source Jitter Compensation | | | | | |
| RMS-Error | 0.04782 | 0.05256 | 0.05930 | 0.07697 | 0.11231 | 0.27941 |
| Correlation | 0.98222 | 0.97852 | 0.97251 | 0.95364 | 0.90084 | 0.70585 |
| | Linear Synthetic Cone Beam Array w/o Source Jitter Compensation | | | | | |
| RMS-Error | 0.04784 | 0.05263 | 0.05949 | 0.07759 | 0.11459 | 0.28473 |
| Correlation | 0.98220 | 0.97846 | 0.97233 | 0.95284 | 0.89637 | 0.69240 |

The local ringing artifacts in linear arrays due to source jitter are highly data dependent, and cases more clearly depicting the advantage of source jitter compensation can be constructed. FIG. 17, however, illustrates that the wobbling artifacts introduced by the geometrical approximations inherent in Feldkamp's cone beam reconstruction algorithm are the predominant cause of the increasing rms-error for growing vertical cone spread angles. The added error in reconstructions from virtual projection data obtained with synthetic cone beam scanner arrays is due to the loss of resolution in resorting the partial projections. As also shown in FIG. 17, the jitter artifacts due to linear arrays does not contribute any substantial reconstruction error.

SECTION 3.3

Vertical Limits of the Artifact-Free Zone

To vertically extend the artifact-free zone of a cone beam scanner, we first evaluate its size associated with the virtual sets of projections yielded by circular and linear synthetic scanner arrays. Once the size, and in particular the height, of the virtual artifact-free zone is determined, a vertical extension is achieved through stacking of the virtual artifact-free zones. Consequently, the scanning procedure due to the synthetic arrays has to be repeated for each of the slices of the artifact-free zone, thus adding a vertical displacement to the displacements in the horizontal XY plane. A resorting approach to the vertical dimension as applied for the horizontal extension of the radius of the artifact-free zone is not pursued here. From the analysis of wobbling artifacts due to the inherent approximations in Feldkamp's cone beam algorithm, it is obvious that any significant extension of the vertical limits of the artifact-free zone will result in an undesired increase of the vertical beam spread. Departing further from the ideal case of parallel projection planes, this approach magnifies the usually minor approximation artifacts and results in an unwanted image degradation. Therefore, we derive the vertical extent of the virtual artifact-free zone due to synthetic scanner arrays, and we use this data to propose a simple straightforward post-reconstruction stacking approach. FIG. 18 illustrates the vertical stacking scheme.

The extend of the virtual artifact-free zone due to circular scanner arrays is straightforward, and is found directly from equations (16) and (17), where we replace $r_o$ by the virtual radius $\tilde{r}_o$. Since for the intermediate slices we cannot use the top and bottom cones as depicted in FIG. 18A, we consider the cylindrical portion of the artifact-free zone only. Thus, for contiguous volume elements we evaluate the height of the stackable slices as $\Delta \tilde{h}_o = \zeta_o (d - \tilde{r}_o)/D$. Clearly we have $$M = \left[ \frac{D \tilde{h}_0}{\zeta_0 (d - \tilde{r}_0)} \right] \tag{28}$$

with M the number of slices needed to cover the required vertical range $\tilde{h}_o$. Thus, the vertical displacements with circular scanner arrays are $$\Delta z_l = \zeta_0 \left( 1 - \frac{M}{2} \right) \frac{d - \tilde{r}_0}{D} \quad \text{for } 0 \leq l < M \tag{29}$$

resulting in the structure depicted in FIG. 18B.

Linear scanner arrays, however, do not yield the simple geometry of the circular case. Evaluation of the vertical extent of the virtual artifact-free zone is complicated by the source jitter in the resorted wedge beam projections as depicted in FIG. 15B. However, the analysis of the source-to-object distance $\psi(s)$ suggests that the artifact-free zones of linear and circular scanner arrays are identical. A proof of the validity of this assumption is provided below (see the following paragraph), where we show that the top and bottom projection planes of the virtual wedge beam do not intersect with the artifact-free zone as depicted in FIG. 12 and FIG. 18A and described by equations (15) through (17). Thus, the simple extension of the vertical limits of the artifact-free zone through stacking proposed for circular scanner arrays is equally applicable to linear arrays.

Figure 19A:
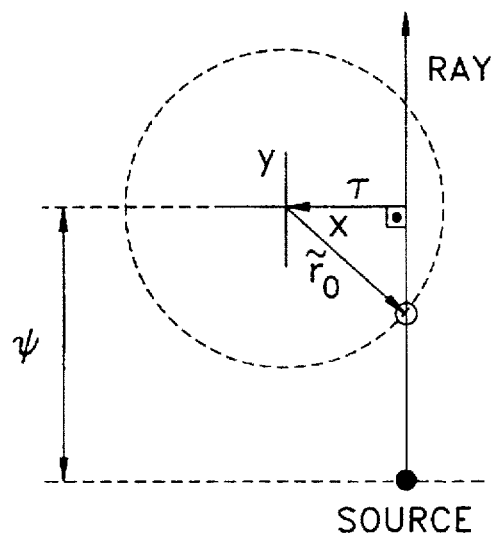
FIGS. 19A and B show the geometric parameters in a set of wedge beam projections resorted from partial sets of cone beam projections in linear scanner arrays. Specifically.
Figure 19B:
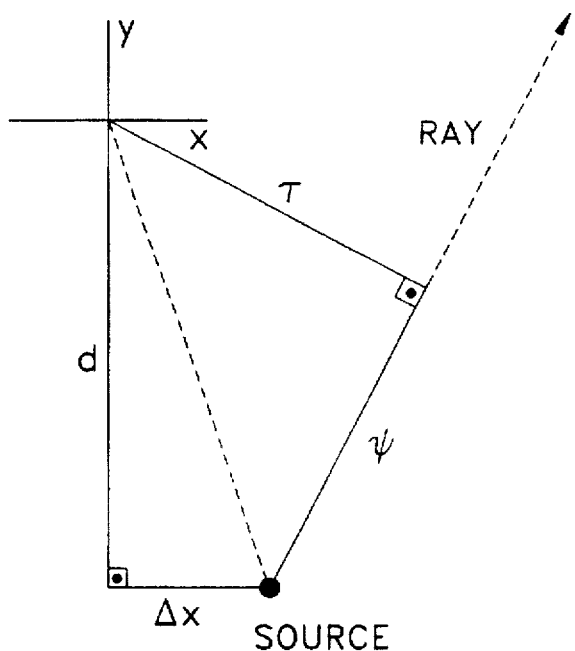

For circular synthetic scanner arrays we evaluate the height of the virtual artifact-free zone as $\tilde{h}_o = \zeta_o (d - \tilde{r}_o)/D$, where we have used the relation $\tilde{h}_o/\zeta_o = (d - \tilde{r}_o)/D$. In order to validate a cylinder with radius $\tilde{r}_o$ and height $\tilde{h}_o$ as the artifact-free zone of three-dimensional linear scanner arrays, we need to show that none of the rays associated with the top and bottom projection planes in the sets of partial projections intersects with this cylinder. From FIG. 19A, we obtain the elevation of an arbitrary ray at the point of crossing the perimeter of the circle with radius $\tilde{r}_o$ as $h = \zeta_o (\psi - \sqrt{\tilde{r}_o^2 - \tau^2})/\sqrt{D^2 + s^2}$. With the geometric identity $d^2 + \Delta x^2 = \tau^2 + \psi^2$ directly from FIG. 19B, we obtain the necessary inequality $$\frac{\sqrt{d^2+\Delta x^2-\tau^2} - \sqrt{\tilde{r}_0^2-\tau^2}}{\sqrt{D^2+s^2}} \geq \frac{d-\tilde{r}_0}{D} \quad (30)$$

From the displacement in linear scanner arrays described by $\Delta_{s,x}=2ks_od/D$ and $k=[\tilde{s}\sqrt{D^2+s_o^2}/(2s_od)]$ as revisited in Section 3.2, we have always $\sqrt{D^2+\tilde{s}^2} \geq \sqrt{D^2+s^2}$ with $\tilde{s}^2$ the detector coordinate of an unbounded detector, while s denotes the detector coordinate associated with the partial projections. Note that $\tilde{s}^2=s$ for the set of partial projections yielded by the center scanner with k=0. From fan beam geometry, we have the ray displacement $\tau=\tilde{s}d/\sqrt{D^2+\tilde{s}^2}$, such that with inversion we change equation (30) to $$\frac{\sqrt{d^2-\tau^2}}{d} \left( \frac{\sqrt{d^2+\Delta x^2-\tau^2} - \sqrt{\tilde{r}_0^2-\tau^2}}{D} \right) \geq \frac{d-\tilde{r}_0}{D} \quad (31)$$

Thus, evaluating the left side for $\Delta x=0$ and rearranging the above equation, we obtain $$\sqrt{d^2-\tau^2} \; (\sqrt{d^2-\tau^2} - \sqrt{\tilde{r}_0^2-\tau^2}) \geq d(d-\tilde{r}_0) \quad (32)$$

with the constraint on $\tau$ as $d > \tilde{r}_o \geq |\tau|$. Differentiating the above equation and setting $d/d\tau=0$ for minimum search, we find one minimum satisfying the constraint on $\tau$ at $$\tau = 0 \rightarrow h_{min} = \zeta_0 \frac{d-\tilde{r}_0}{D} \quad (33)$$

which is identical to $\tilde{h}_o$ as stated in the beginning of the proof. The validation of the cylindric portion of the artifact-free zone due to circular scanner arrays as the artifact-free zone due to linear scanner arrays is therefore complete.

Therefore, the preferred methods of the present invention include:

1) a scanning and data acquisition method for 3-D cone beam computerized tomography (CT) imaging of an object within a field of view, said method comprising:

providing a cone beam x-ray source and a detector array having a total area which is insufficient to contain the field of view;

successively scanning said object and acquiring partial cone-beam x-ray data sets at a plurality of relative positions of said object and said x-ray source and detector array, said object being translated along the x and y axes, and optionally the z-axis, and rotated through a rotation angle of 360° relative to said x-ray source and detector array at every position, the translations in effect building a circular synthetic detector array around the object;

combining said partial data sets to yield a full data set covering the entire field of view from which to reconstruct an image of said object.

2) a scanning and data acquisition method for 3-D cone beam computerized tomography (CT) imaging of an object within a field of view, said method comprising:

providing a cone beam x-ray source and a detector array having a total area which is insufficient to contain the field of view;

successively scanning said object and acquiring partial cone-beam x-ray data sets at a plurality of relative positions of said object and said x-ray source and detector array, said object being translated along the x axis, and optionally the z-axis, and rotated through a rotation angle of 360° relative to said x-ray source and detector array at every position, the translations in effect building a planar synthetic detector array;

combining said partial data sets to yield a full data set covering the entire field of view from which to reconstruct an image of the object.

SECTION 4

Further Detailed Description of the Present Invention

To better understand the impact of the projection geometry on the reconstruction process, a short review in tomographic scanning and reconstruction is provided. In standard fan- or cone-beam tomography, the source, the object's center of rotation, and the center of the detector have to be precisely aligned on a straight line. Displacing the detector center relative to the axis of object rotation merely requires some simple preprocessing (e.g., interpolation, averaging, or simply patching together disjoint projections) because neither the projection geometry nor the projection's information content is changed. Displacing the source relative to the axis of object rotation, however, changes the projection geometry and requires a much more complex preprocessing of the projection data. As long as the information contained in the projections is completely describing the imaged object, however, this preprocessing may rearrange the information in the projection space without adding or removing any information. Thus, the projections can be remapped to a standard scanning geometry and subsequently be reconstructed with standard algorithms (such as the fan beam backprojection for two-dimensional tomography, for instance), which expect the information in the projections to be arranged in a particular fashion. The advantages of using non-standard projection geometries may improve accuracy, reconstruction speed, artifact and noise robustness, linearity, etc., depending on the various parameters.

In two-dimensional fan beam tomography, untruncated projections completely describe the scanned object. Thus, an object may be scanned using any variation of the fan beam geometry, provided the projections can be mapped to the standard fan or parallel beam geometry and subsequently reconstructed using the appropriate standard algorithm.

In three-dimensional cone beam tomography, true three-dimensional algorithms reconstructing from projections completely describing the investigated object are not used in practice, since they require complex scanning setups rotating the object in two or more axes. Also, true three-dimensional reconstruction algorithms suffer from excessive memory consumption and unacceptable reconstruction runtimes.

Practical algorithms avoid these problems by reconstructing an approximate image from projections only almost completely describing the object. The most widely used practical three-dimensional reconstruction method, Feldkamp's cone beam algorithm, reconstructs from (inherently incomplete) cone beam projections. The algorithm very well utilizes the available information to generate fairly good but only approximate reconstructions of the object.

Since cone beam projections are inherently incomplete, the projection geometry may not be varied to achieve a certain effect on the data obtained in the scanning process. Remapping projections obtained in a non-standard cone beam geometry to a standard cone beam format results in gaps in the projection space, causing severe image artifacts. Thus, any departure from the standard cone beam geometry necessitates a dedicated reconstruction algorithm.

In the linear method proposed in the present patent application, the source and detector (or equivalently, the object) are displaced. Displacing the source relative to the axis of object rotation changes the projection geometry, such that Feldkamp's cone beam algorithm can no longer be used for reconstruction. Instead, a wedge beam algorithm has been devised, which is capable of forming an approximate image from the preprocessed projections, comparable in accuracy to images reconstructed with Feldkamp's algorithm.

SECTION 4.1

Further Teachings Regarding the Linear Method

In the linear method of the present patent application, the detector and the source are displaced relative to the axis of object rotation. The source may remain aligned with the detector center, it may be displaced from both the axis of object rotation and the detector center.

In the linear method of the present patent application, the reconstruction algorithm used to form the object image is a dedicated wedge beam algorithm. The advantage in using the method of the present invention is the increased size of the virtual detector, or the larger effective field of view.

SECTION 4.2

Variations in the Linear Method

Assuming that the scanning device has a source and a detector situated at the opposite ends of a shielding box, the following variables are used:

W Width of the shielding box.

D Length of the shielding box (distance from the source to detector)

d Distance from source to object's center of rotation.

s Physical size of the detector from center to end (the detector width is thus 2s).

s' Effective size of the virtual detector from center to end (the virtual detector width is thus 2s').

r' Radius of the zone of reconstruction (any object has to fit entirely into that zone to yield untruncated reconstructions).

In the linear method proposed in the present patent application, a set of variations may be claimed with different costs and performances. In variations (a), (b), and (c), the actual displacements between detector/source and the object turntable are identical, but are implemented in different fashions.

Figure 20:
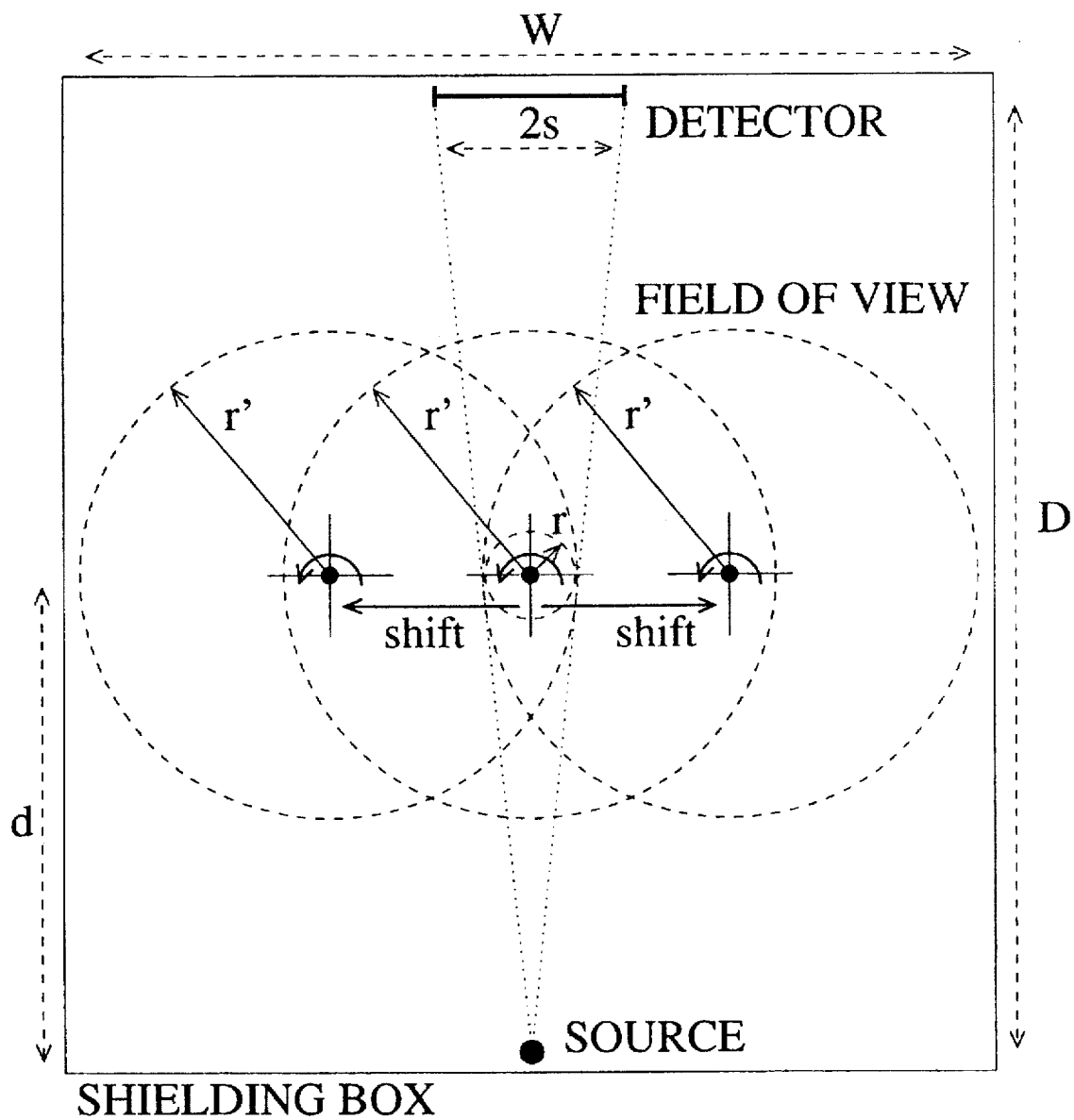
FIG. 20 is a cross-sectional side view of a shielding box of the type used for variation (a) of the linear cone beam scanner array.

(a) This variation horizontally displaces the object turntable, while the source and detector remain stationary at the center of the bottom and the top of the box, respectively (see FIG. 20). This variation requires one linear axis. The precise turntable displacements are described in earlier sections of the present patent application.

Figure 21:
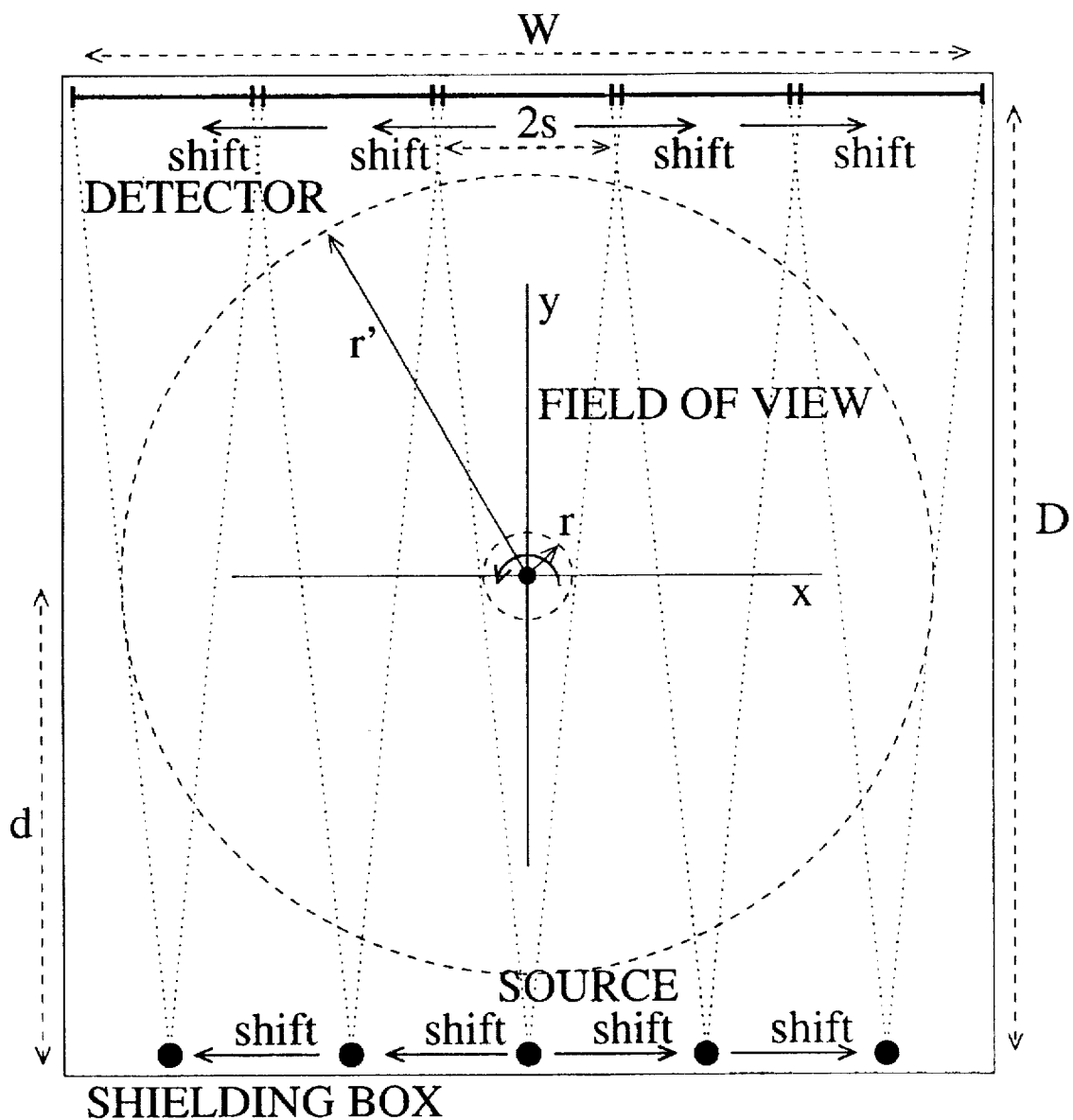
FIG. 21 is a cross-sectional side view of a shielding box of the type used for variation (b) of the linear cone beam scanner array.

(b) This variation horizontally displaces the source and detector situated at the bottom and the top of the box, where the source and detector centers remain aligned at all times; the object turntable remains stationary at all times (see FIG. 21). This variation requires two linear axes. The actual source/detector-to-turntable displacements are identical to the displacements on variation (a).

Figure 23:
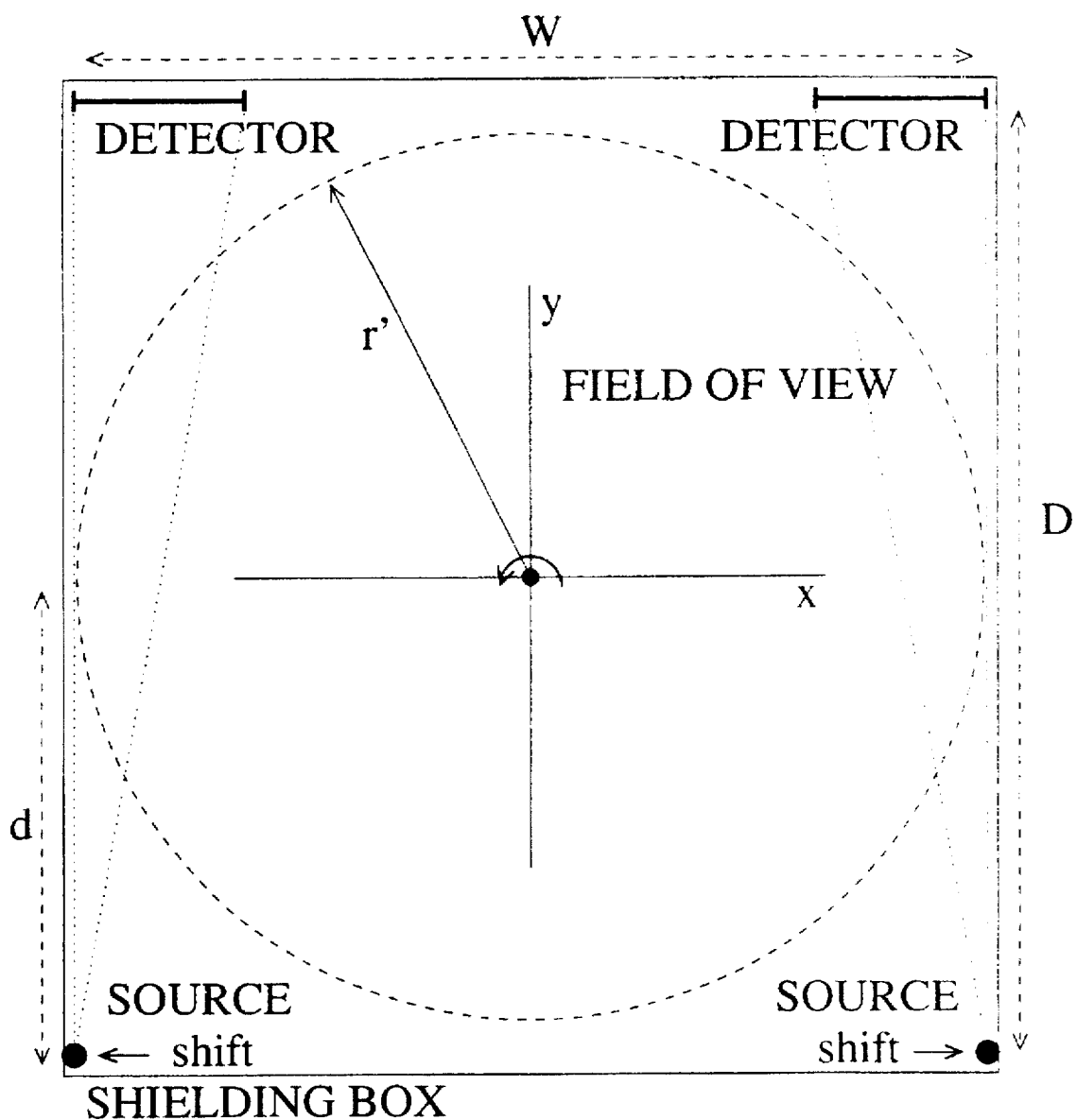
FIG. 23 is a cross-sectional side view of a shielding box of the type used for variations (b2) and (c2) of the linear cone beam scanner array.

(b2) This variation is identical to variation (b), except that two additional scans are recorded at the left and right outmost source positions. In variation (b), the left/rightmost scans had the detector placed at the far left/right of the box and the source horizontally aligned with the center of the detector. For the additional scans, the detector remains at the far left/right, but the source is shifted out of the detector center to the far left/right. Thus, for the additional scans the source is no longer aligned with the detector center. Instead it is aligned with the left/right detector ends. With these additional scans radius r' equals W/2, independent of D, d, and s (see FIGS. 21 and 23).

Figure 22:
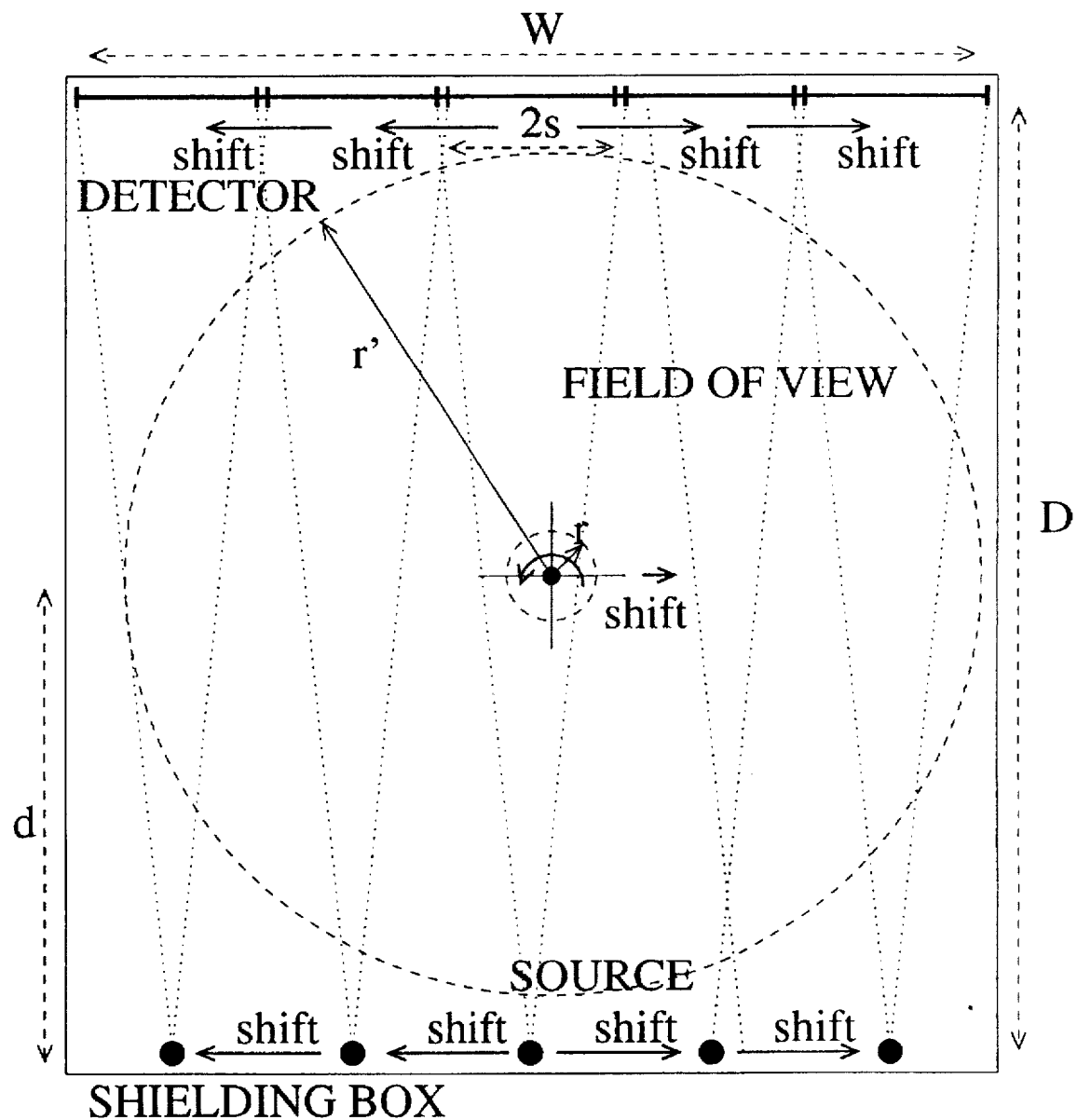
FIG. 22 is a cross-sectional side view of a shielding box of the type used for variation (c) of the linear cone beam scanner array.

(c) This variation horizontally displaces the source and detector situated at the bottom and top of the box to one side of the box, while at the same time horizontally displaces the object turntable situated at a distance d from the bottom of the box to the opposite side of the box (see FIG. 22). This variation requires three linear axes. The source and detector centers remain aligned at all times. The actual source/detector-to-turntable displacements are identical to the displacements in variations (a) and (b).

(c2) The principle of (b2) applied to variation (c). This variation is identical to variation (c), except that two additional scans are recorded at the left and right outmost source positions. In variation (c), the left/rightmost scans had the detector placed at the far left/right of the box and the source horizontally aligned with the center of the detector. For the additional scans, the detector remains at the far left/right, but the source is shifted out of the detector center to the far left/right. Thus, for the additional scans the source is no longer aligned with the detector center. Instead, it is aligned with the left/right detector ends. With these additional scans radius r' equals W/2, independent of D,d, and s (see FIGS. 22 and 23).

For all variations, the same signal processing applies. Thus, for variations (a), (b), and (c), with the source aligned with the detector center, the radius r' is computed as $$r'(D,d,s,x) = \frac{sd + xD}{\sqrt{D^2 + s^2}} \tag{34}$$

while for variations (b2) and (c2), with the source aligned with the detector ends for the additional outmost scans, the radius r' is always $$r'=0.5. \tag{35}$$

Here, x denotes the maximum source/detector to object displacement. Since the method proposed in the present patent application may yield a field of view extending beyond the limits of the shielding box, the object may collide with the source, the detector, or the walls of the shielding box. For all practical purposes we will assume that the object does not collide with the source or detector, and we only have to be careful not to collide with the walls of the shielding box (meaning the box is longer than wide). For variation (a), we have $x \leq W/2 - r'$. Thus, $$r'(W,D,d,s) = \frac{sd + WD/2}{D + \sqrt{D^2 + s^2}}. \tag{36}$$

For variation (b), we have $x \leq W/2 - s$. Thus, $$r'(W,D,d,s) = \frac{sd + WD/2 - sD}{\sqrt{D^2 + s^2}}. \tag{37}$$

For variation (c), we have $x \leq W - r' - s$. Thus, $$r'(W,D,d,s) = \frac{sd + WD - sD}{D + \sqrt{D^2 + s^2}}. \tag{38}$$

In a practical application, one would have an existing shielding box of dimensions W and D, a source and detector located at the center of the bottom and the top of the box, respectively, and a horizontally centered turntable situated at distance d from the source. According to the variations (a), (b), and (c), one would pick the variation which yields the greatest radius r' at the least cost, whatever yields the optimum depending on the applied cost function.

Variation (a) does well with larger detectors (s approaching W/2) while variation (b) does well with smaller detectors (s approaching 0). Variation (c) is superior to either (a) or (b), but incorporates a higher cost (three linear axes). Variations (b2) and (c2) always yield the maximum radius r'.

Variations (b) and (b2) seem to yield the best performance-to-cost ratios. These variations require two linear axes to shift the detector and the source, and yield very good fields of view. By recording two additional scans at outmost source positions, (b2) yields the maximum field of view, limited in extent only by the walls of the shielding box.

Table 3 shows several examples of the radius r' of the field of view as a function of box width W, box height D, distance d from source to axis of object rotation, and detector size s.

TABLE 3

| Parameters | | Radius r' | | | | |
|---|---|---|---|---|---|---|
| W,D,d | s | (a) | (b) | (b2) | (c) | (c2) |
| W = 1.0 | 0.01 | 0.25249 | 0.49498 | 0.50000 | 0.49749 | 0.50000 |
| D = 1.0 | 0.1 | 0.27431 | 0.44777 | 0.50000 | 0.47382 | 0.50000 |
| d = 0.5 | 0.25 | 0.30776 | 0.36380 | 0.50000 | 0.43087 | 0.50000 |
| | 0.4 | 0.34913 | 0.29851 | 0.50000 | 0.38516 | 0.50000 |
| | 0.5 | 0.35410 | 0.22361 | 0.50000 | 0.35410 | 0.50000 |
| W = 1.0 | 0.01 | 0.25250 | 0.49500 | 0.50000 | 0.49750 | 0.50000 |
| D = 2.0 | 0.1 | 0.27483 | 0.44944 | 0.50000 | 0.47470 | 0.50000 |
| d = 1.0 | 0.25 | 0.31129 | 0.37210 | 0.50000 | 0.43580 | 0.50000 |
| | 0.4 | 0.34657 | 0.29417 | 0.50000 | 0.39608 | 0.50000 |
| | 0.5 | 0.36932 | 0.24254 | 0.50000 | 0.36932 | 0.50000 |
| W = 1.0 | 0.01 | 0.25125 | 0.49249 | 0.50000 | 0.49625 | 0.50000 |
| D = 2.0 | 0.1 | 0.26234 | 0.42447 | 0.50000 | 0.46221 | 0.50000 |
| d = 0.5 | 0.25 | 0.28016 | 0.31009 | 0.50000 | 0.40468 | 0.50000 |
| | 0.4 | 0.29706 | 0.19617 | 0.50000 | 0.34657 | 0.50000 |
| | 0.5 | 0.30776 | 0.12127 | 0.50000 | 0.30776 | 0.50000 |
| W = 1.0 | 0.01 | 0.25375 | 0.49749 | 0.50000 | 0.49875 | 0.50000 |
| D = 2.0 | 0.1 | 0.28732 | 0.47441 | 0.50000 | 0.48720 | 0.50000 |
| d = 1.5 | 0.25 | 0.34242 | 0.43412 | 0.50000 | 0.46693 | 0.50000 |
| | 0.4 | 0.39608 | 0.39223 | 0.50000 | 0.44559 | 0.50000 |
| | 0.5 | 0.43087 | 0.36380 | 0.50000 | 0.43087 | 0.50000 |

While the invention has been particularly shown and described with reference to preferred embodiments thereof, it will be understood by those skilled in the art that various changes in form and details may be made without departing from the spirit and scope of the invention as defined in the appended claims.

What is claimed is:

1. A scanning and data acquisition method for 3-D cone beam computerized tomography (CT) imaging of an object within a field of view, said method comprising:

providing a cone beam x-ray source and a detector array having a total area which is insufficient to contain the field of view;

successively scanning said object and acquiring partial cone-beam x-ray data sets at a plurality of relative positions of said object and said x-ray source and detector array, said object being translated along the x and y axes, and optionally the z-axis, and rotated through a rotation angle of 360° relative to said x-ray source and detector array at every position;

combining said partial data sets to yield a full data set covering the entire field of view from which to reconstruct an image of said object.

2. A scanning and data acquisition method for 3-D cone beam computerized tomography (CT) imaging of an object within a field of view, said method comprising:

providing a cone beam x-ray source and a detector array having a total area which is insufficient to contain the field of view;

successively scanning said object and acquiring partial cone-beam x-ray data sets at a plurality of relative positions of said object and said x-ray source and detector array, said object being translated along the x axis, and optionally the z-axis, and rotated through a rotation angle of 360° relative to said x-ray source and detector array at every position;

combining said partial data sets to yield a full data set covering the entire field of view from which to reconstruct an image of said object.

3. A scanning and data acquisition method for 3-D cone beam computerized tomography (CT) imaging of an object within a field of view, said method comprising:

providing a cone beam x-ray source and a detector array having a total area which is insufficient to contain the field of view;

successively scanning said object and acquiring partial cone-beam x-ray data sets at a plurality of relative positions of said object and said x-ray source and detector array, wherein said x-ray source and detector array are horizontally displaced simultaneously while the object remains stationary and said object being rotated through a rotation angle of 360° relative to said x-ray source and detector array at every position, said horizontal displacement of said x-ray source having a range which is limited by left and right limits for the x-ray source and said horizontal displacement of said detector array having a range which is limited by left and right limits for the detector array;

combining said partial data sets to yield a full data set covering the entire field of view from which to reconstruct an image of said object.

4. The scanning and data acquisition method of claim 3, wherein said object, said x-ray source and said detector array are all contained within a shielding box having a left wall and a right wall, further wherein said x-ray source has a leftmost end, a center and a rightmost end, and said detector array has a leftmost end, a center and a rightmost end, said method including the step of scanning the object when the relative positions of the object, the detector array and the x-ray source are such that the leftmost end of said x-ray source is in contact with or nearly in contact with the left wall of said shielding box and the center of said x-ray source is in alignment with the leftmost end of said detector array which is located at the left limit of the detector array, and said method also including the step of scanning the object when the relative positions of the object, the detector array and the x-ray source are such that the rightmost end of said x-ray source is in contact with or nearly in contact with the right wall of said shielding box and the center of said x-ray source is in alignment with the rightmost end of said detector array which is located at the right limit of the detector array.

5. The scanning and data acquisition method of claim 3, wherein said x-ray source has a center and said detector array has a center and the center of said x-ray source is maintained in alignment with the center of said detector array during said simultaneous horizontal displacement.

6. The scanning and data acquisition method of claim 5, wherein after scans have been performed at the left and right limits of the detector array with the center of the x-ray source in alignment with the center of the detector array, two additional scans are carried out at the left and right limits of the x-ray source with the center of the x-ray source being out of alignment with the center of the detector array.

7. The scanning and data acquisition method of claim 6, wherein said detector array has a leftmost end and a rightmost end and further wherein during the two additional scans which are carried out at the left and right limits of the x-ray source, when the scan at the left limit of the x-ray source is performed, the center of the x-ray source is aligned with the leftmost end of the detector array and when the scan at the right limit of the x-ray source is performed, the center of the x-ray source is aligned with the rightmost end of the detector array.

8. A scanning and data acquisition method for 3-D cone beam computerized tomography (CT) imaging of an object within a field of view, said method comprising:

providing a cone beam x-ray source and a detector array having a total area which is insufficient to contain the field of view;

successively scanning said object and acquiring partial cone-beam x-ray data sets at a plurality of relative positions of said object and said x-ray source and detector array, wherein said x-ray source and detector array are horizontally displaced simultaneously in one direction while the object is horizontally displaced in the opposite direction and said object being rotated through a rotation angle of 360° relative to said x-ray source and detector array at every position, said horizontal displacement of said x-ray source having a range which is limited by left and right limits for the x-ray source and said horizontal displacement of said detector array having a range which is limited by left and right limits for the detector array;

combining said partial data sets to yield a full data set covering the entire field of view from which to reconstruct an image of said object.

9. The scanning and data acquisition method of claim 8, wherein said object, said x-ray source and said detector array are all contained within a shielding box having a left wall and a right wall, further wherein said x-ray source has a leftmost end, a center and a rightmost end, and said detector array has a leftmost end, a center and a rightmost end, said method including the step of scanning the object when the relative positions of the object, the detector array and the x-ray source are such that the leftmost end of said x-ray source is in contact with or nearly in contact with the left wall of said shielding box and the center of said x-ray source is in alignment with the leftmost end of said detector array which is located at the left limit of the detector array, and said method also including the step of scanning the object when the relative positions of the object, the detector array and the x-ray source are such that the rightmost end of said x-ray source is in contact with or nearly in contact with the right wall of said shielding box and the center of said x-ray source is in alignment with the rightmost end of said detector array which is located at the right limit of the detector array.

10. The scanning and data acquisition method of claim 8, wherein said x-ray source has a center and said detector array has a center and the center of said x-ray source is maintained in alignment with the center of said detector array during said simultaneous horizontal displacement.

11. The scanning and data acquisition method of claim 10, wherein after scans have been performed at the left and right limits of the detector array with the center of the x-ray source in alignment with the center of the detector array, two additional scans are carried out at the left and right limits of the x-ray source with the center of the x-ray source being out of alignment with the center of the detector array.

12. The scanning and data acquisition method of claim 11, wherein said detector array has a leftmost end and a rightmost end and further wherein during the two additional scans which are carried out at the left and right limits of the x-ray source, when the scan at the left limit of the x-ray source is performed, the center of the x-ray source is aligned with the leftmost end of the detector array and when the scan at the right limit of the x-ray source is performed, the center of the x-ray source is aligned with the rightmost end of the detector array.

* * * * *

UNITED STATES PATENT AND TRADEMARK OFFICE
CERTIFICATE OF CORRECTION

PATENT NO. : 5,740,224
DATED : April 14, 1998
INVENTOR(S) : Martin Muller, et al.

It is certified that error appears in the above-identified patent and that said Letters Patent is hereby corrected as shown below:

On the cover page in section [54], the word "SCANNER" should be inserted between the words "SYNTHETIC" and "ARRAYS".

Signed and Sealed this

Sixth Day of October, 1998

*Attest:*

BRUCE LEHMAN

*Attesting Officer*            *Commissioner of Patents and Trademarks*